(12) United States Patent
Shimokawa et al.

(10) Patent No.: US 9,857,391 B2
(45) Date of Patent: Jan. 2, 2018

(54) PLANT WATER DYNAMICS SENSOR

(71) Applicant: NATIONAL UNIVERSITY CORPORATION KAGAWA UNIVERSITY, Kagawa (JP)

(72) Inventors: Fusao Shimokawa, Kagawa (JP); Hidekuni Takao, Kagawa (JP); Takaaki Suzuki, Kagawa (JP); Tsuyoshi Kobayashi, Kagawa (JP); Ikuo Kataoka, Kagawa (JP)

(73) Assignee: NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 0 days.

(21) Appl. No.: 15/115,866

(22) PCT Filed: Jan. 26, 2015

(86) PCT No.: PCT/JP2015/000325
§ 371 (c)(1),
(2) Date: Aug. 1, 2016

(87) PCT Pub. No.: WO2015/115084
PCT Pub. Date: Aug. 6, 2015

(65) Prior Publication Data
US 2017/0010296 A1    Jan. 12, 2017

(30) Foreign Application Priority Data
Feb. 3, 2014    (JP) .................................. 2014-018226

(51) Int. Cl.
*G01P 5/12*    (2006.01)
*A01G 25/16*    (2006.01)
(Continued)

(52) U.S. Cl.
CPC ................. *G01P 5/08* (2013.01); *A01G 1/001* (2013.01); *A01G 7/06* (2013.01); *A01G 25/16* (2013.01);
(Continued)

(58) Field of Classification Search
None
See application file for complete search history.

(56) References Cited

U.S. PATENT DOCUMENTS 5,367,905 A * 11/1994 Senock ................. G01F 1/6847
                                                            73/204.22
5,423,211 A *  6/1995 Senock ..................... G01F 1/68
                                                            73/204.22

FOREIGN PATENT DOCUMENTS

JP    H06-273434 A    9/1994
JP    2008-233047 A   10/2008
WO    2015/006675 A2   1/2015

OTHER PUBLICATIONS

International Search Report for PCT/JP2015/000325, dated Feb. 17, 2015.
(Continued)

*Primary Examiner* — Harshad R Patel

(57) ABSTRACT

A plant water dynamics sensor usable for measuring the dynamics of water flowing in a fine point of a plant such as a distal end of a new branch or a pedicel comprises a heater-equipped temperature probe including a temperature sensor and a heater; a temperature probe including a temperature sensor; an electrical resistance probe including an electrical resistance measurement electrode; and a support that supports the probes while the probes are aligned parallel to each other. The position of a xylem XY can be detected based on an electrical resistance measured at the electrical resistance probe, so that each of the temperature sensors can be arranged correctly in a position at a phloem PH or at the
(Continued)

xylem XY. This facilitates attachment of a plant water dynamics sensor and water dynamics in a plant can be measured with high accuracy.

9 Claims, 24 Drawing Sheets

(51) Int. Cl.
*G01P 5/08* (2006.01)
*A01G 1/00* (2006.01)
*A01G 7/06* (2006.01)
*G01N 33/00* (2006.01)

(52) U.S. Cl.
CPC ....... *A01G 25/167* (2013.01); *G01N 33/0098* (2013.01); *G01P 5/12* (2013.01)

(56) References Cited

OTHER PUBLICATIONS

Written opinion of the International Searching Authority for PCT/JP2015/000325, dated Feb. 17, 2015.
Makoto Ochi et al., "Fabrication of micro sap flow sensor by using MEMS technology", The 29th Sensor Symposium on Sensors, Micromachines and Applied Systems, Oct. 22, 2012, p. 173, Toshio Shimada Secretary, IEEJ, Japan.
European Patent Office, Extended European Search Report for EP Patent Application No. 15743603.1, Sep. 20, 2017.

\* cited by examiner

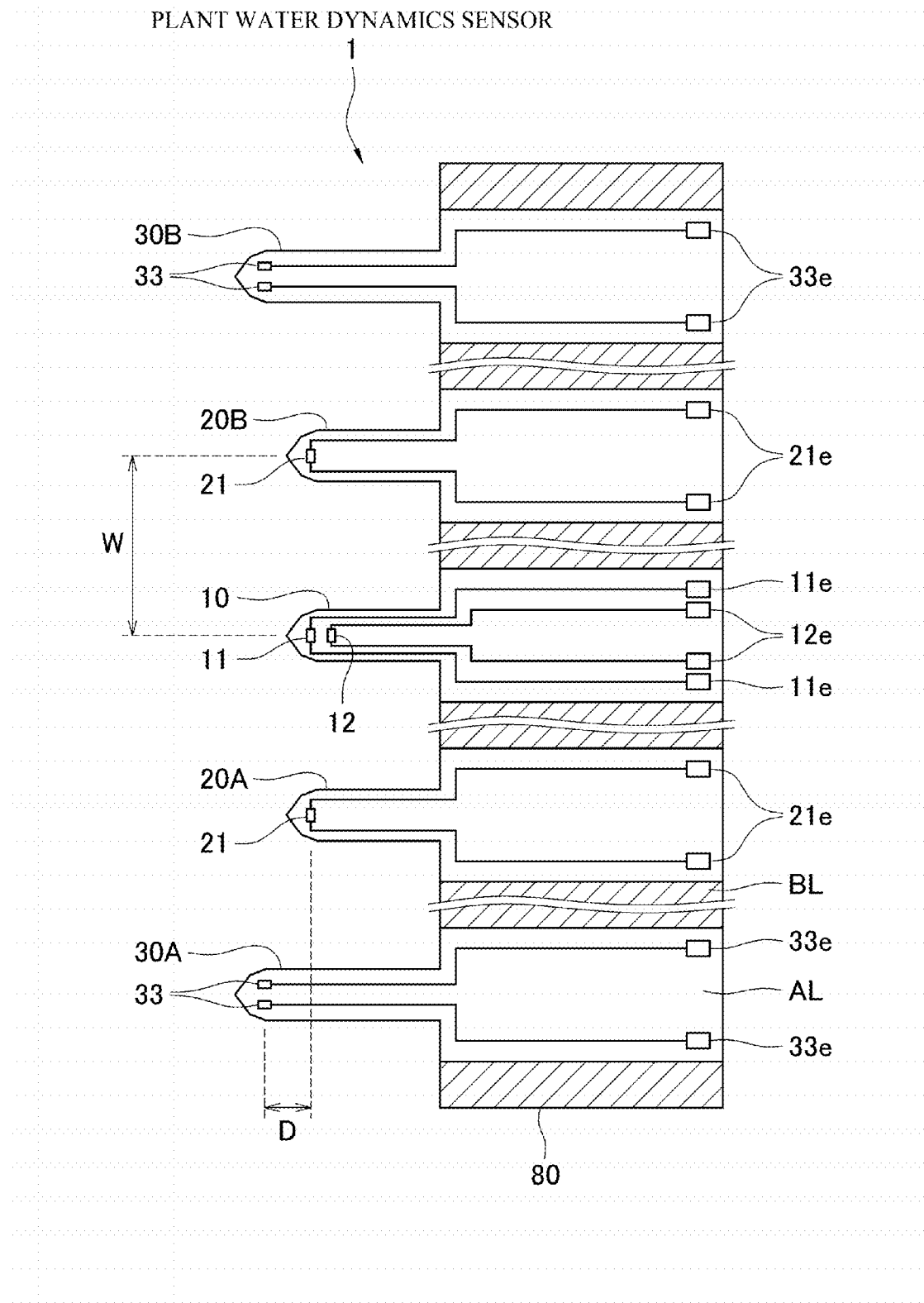

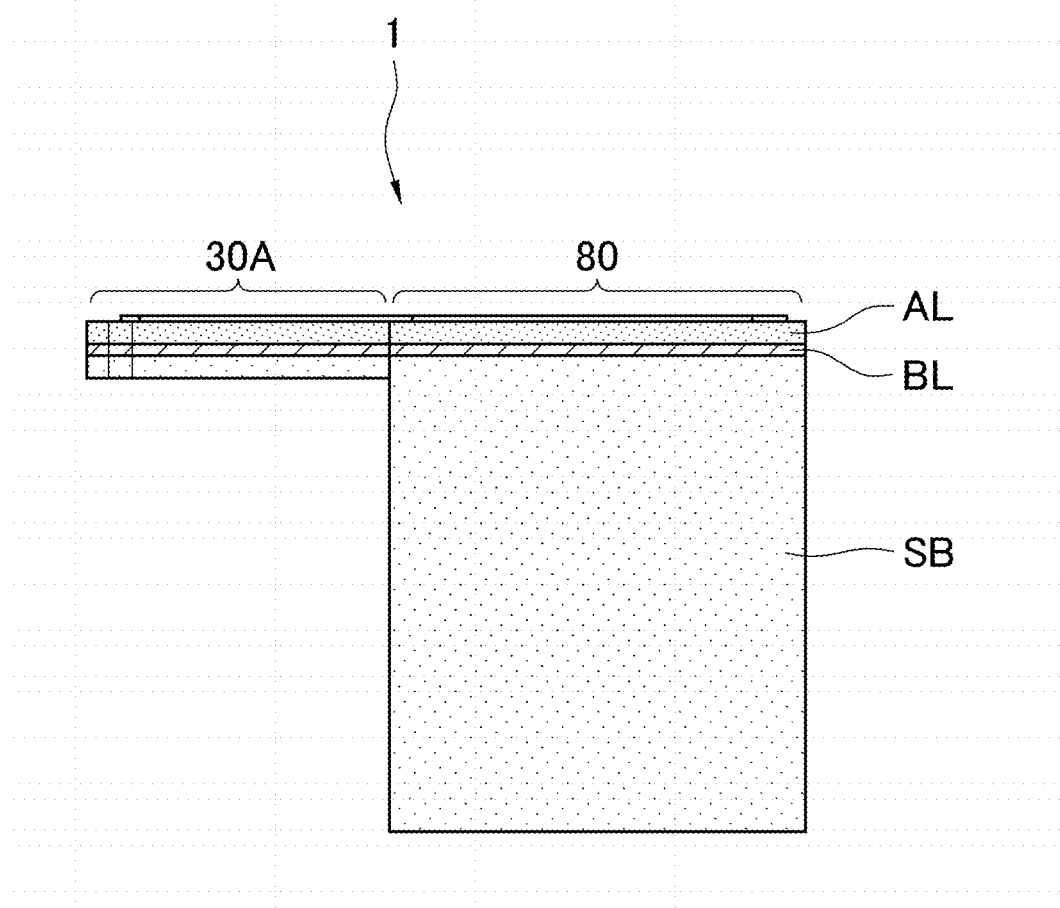

F I G. 1 7
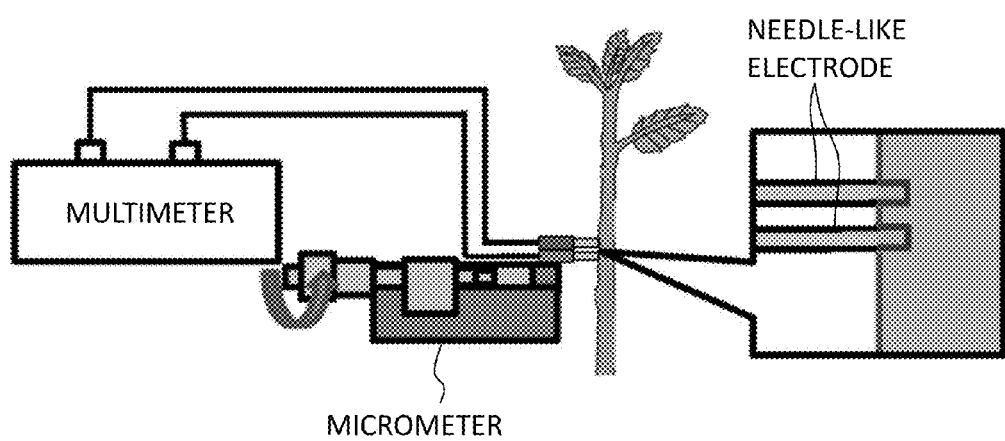

F I G. 1 8
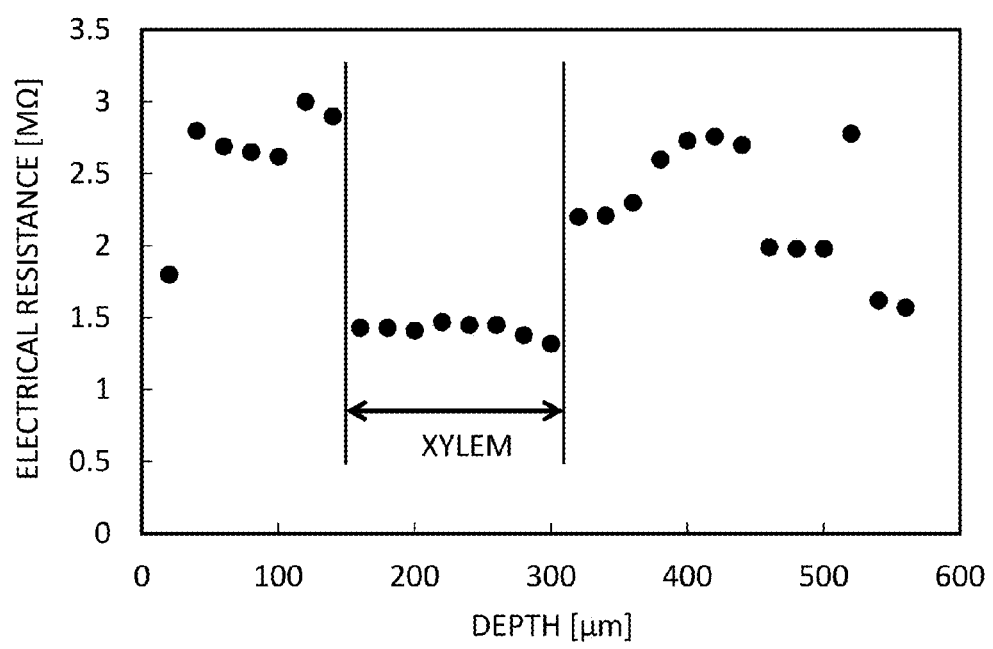

F I G. 1 9
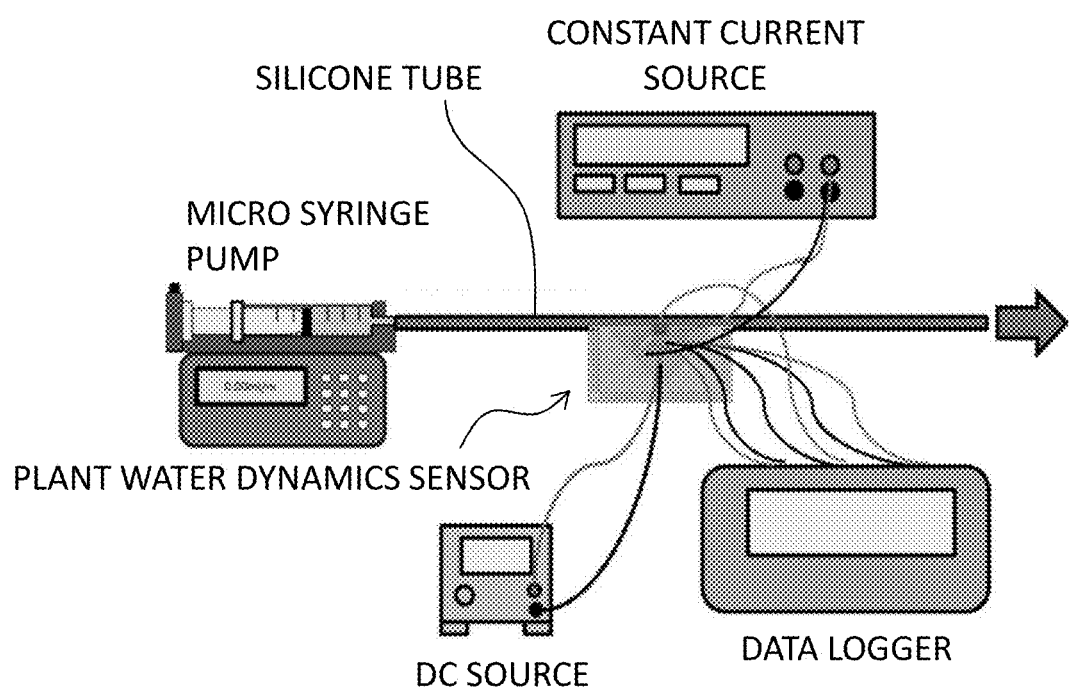

F I G. 2 1
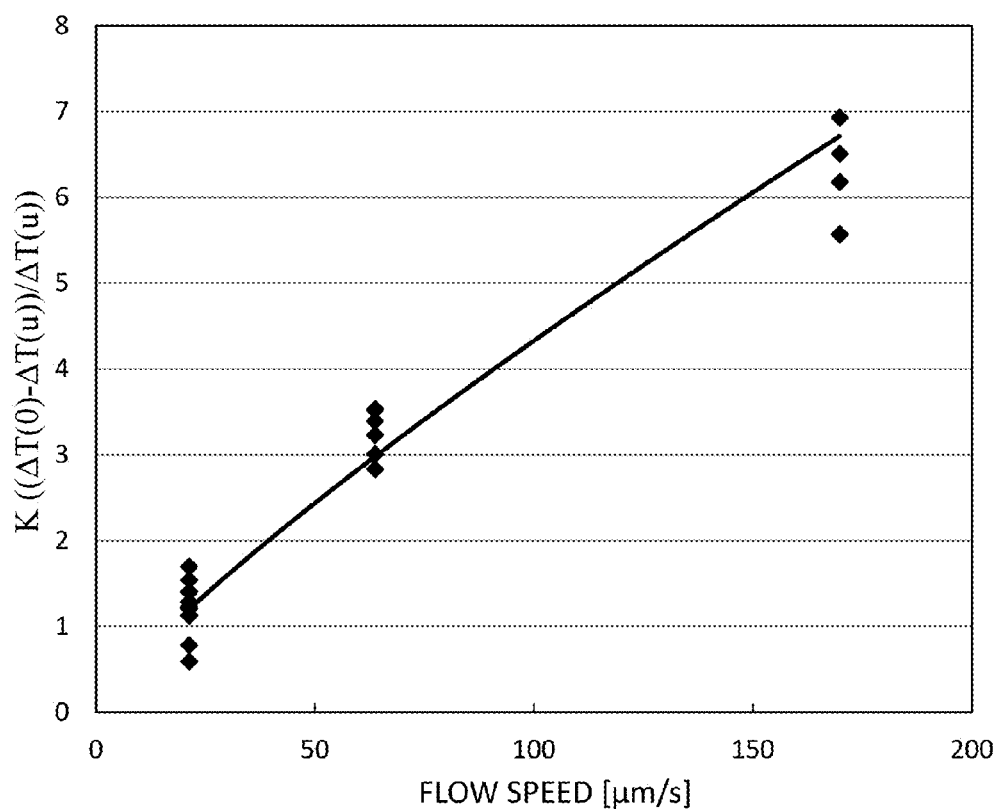

F I G. 2 3
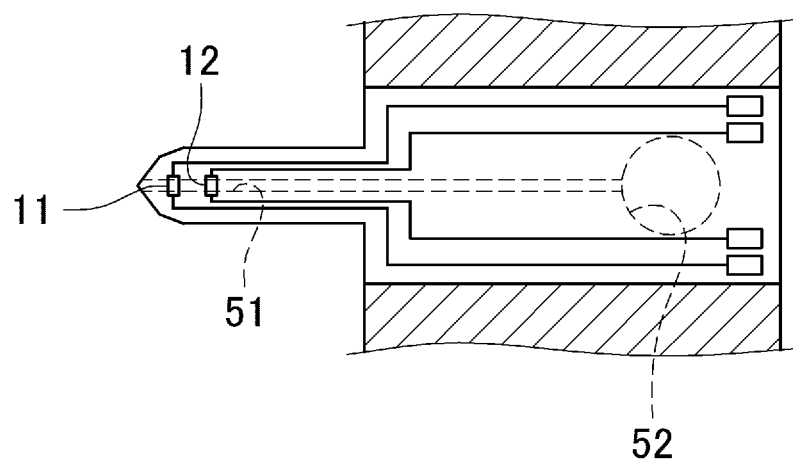

F I G. 2 4
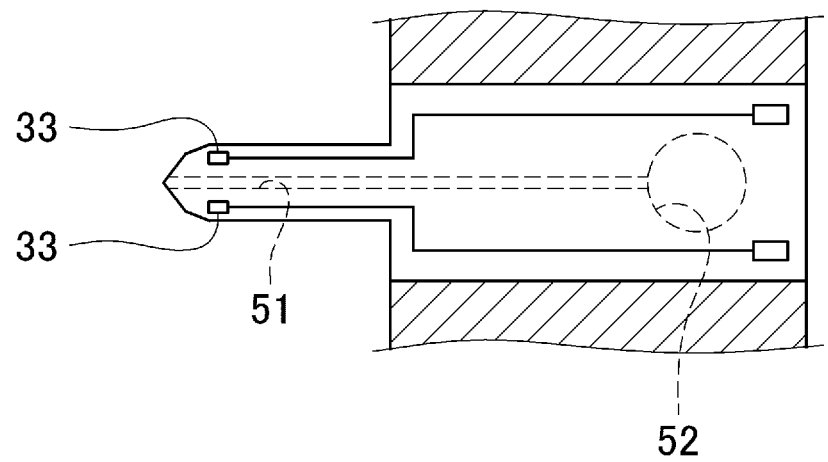

PLANT WATER DYNAMICS SENSOR

TECHNICAL FIELD

This invention relates to a plant water dynamics sensor. More specifically, this invention relates to a plant water dynamics sensor usable for measuring water dynamics in a fine point of a plant such as a distal end of a new branch.

BACKGROUND ART

In the cultivations of crops, fruit, and the like, plants should be supplied with water and nutrients in terms of productivity at appropriate times based on the growing status of the plants. Thus, grasping the growing status of the plants properly without affecting growing of the plants is essentially important.

In many actual situations in the present agricultural fields, the growing status of plants is grasped according to human experience based on the number of days without rain or by intuition, for example. However, managing the growing status of plants by a method based on experience, and the like is skillful work that involves much expense in time and effort. Additionally, barometers as a reference in such management are determined from personal experiences, for example. Hence, not everyone finds it easy to implement such a method of grasping the growing status of plants based on experience, etc.

On the other hand, various techniques have been developed in recent years intended to execute water control or fertilization management of crops or fruit based on biological information of a plant. Among these techniques, a measuring method using the Granier method is a notable method. This method is to enable grasp of biological information of a plant more correctly as it allows a sap flow of the plant to be measured directly (see patent literature 1, for example).

Patent literature 1 discloses a device with a rod-shaped temperature sensor and a rod-shaped heater-equipped sensor that can be arranged in holes formed in the trunk of a tree with a drill, for example. According to a technique disclosed in patent literature 1, both of these sensors of the device are arranged in the holes formed in a sapwood part of a tree. After elapse of a predetermined time, the flow rate of sap flowing in the tree is determined based on a temperature difference between these sensors.

The device of patent literature 1 has originally been developed for measurement of a tree having a large stem diameter (more specifically, a stem diameter of 20 cm or more). The rod-shaped sensors used in the device are formed into a size from 2 or 3 mm or more in diameter and from 2 to 3 cm or more in length. Thus, the device of patent literature 1 is not applicable to a plant having a stem diameter of less than 20 cm. Additionally, for measurement of a sap flow rate, this device requires formation of a hole in a tree with a drill, for example. Hence, a sap flow rate cannot be measured using the device of patent literature 1 unless a few days have elapsed after installation of the device. Further, chipping off the epidermis of a tree, forming holes in the tree with a drill, and inserting the sensors is destructive testing.

A device also applicable to a plant having a small stem diameter has been developed (see patent literature 2). Patent literature 2 discloses a stem liquid flow measurement sensor formed of a thin-film base rectangular in a plan view and having a longitudinal length (lengthwise direction) from about 15 to 20 mm, a crosswise length of about 10 mm, and a thickness from about several hundreds of micrometers to 1 mm. This stem liquid flow measurement sensor includes a thin-film temperature-measurement metallic resistive elements in a pair formed on the base and a thin-film metallic heater provided between these resistive elements in a pair. According to the recitation of patent literature 2, the stem liquid flow measurement sensor is inserted to about two-thirds from its surface in the lengthwise direction into a cut formed in the axis direction of the stem of a tomato. Then, this sensor is arranged in such a manner that the resistive elements and a heater are arranged in a xylem inside the stem. In this way, a stem liquid flow can be measured while adverse effect on a plant is reduced.

PRIOR ART LITERATURES

Patent Literatures

Patent Literature 1: Japanese Patent Application Publication No. H6-273434

Patent Literature 2: Japanese Patent Application Publication No. 2008-23304

SUMMARY OF INVENTION

Problem to be Solved by Invention

As described above, measuring a sap flow rate in a plant directly is important for grasping the growing status of the plant. In particular, measuring movement of water (specifically, water dynamics) in a fine point of a plant having a diameter of about several millimeters such as a distal end of a new branch or a pedicel of a plant existing near a crop or a fruit is considerably important for enhancing the productivity and the quality of crops, fruit, and the like.

The stem liquid flow measurement sensor of patent literature 2 has a smaller size than the device of patent literature 1, so that this sensor is also applicable to a plant having a stem diameter of less than 20 cm. During attachment of the sensor of patent literature 2 to a plant, a point as a measurement target is not destroyed seriously, compared to the device of patent literature 1. Meanwhile, the stem liquid flow measurement sensor of patent literature 2 involves formation of a cut of about 20 mm long and from about 5 to 10 mm deep in a stem, so that this sensor cannot be attached for example to a distal end of a new branch having a stem diameter of several millimeters. Even if the sensor of patent literature 2 can be attached to a point such as a distal end of a new branch that becomes an important point for growing of a plant, the attachment causes the aforementioned flaw in this point. This flaw may cause infection or dieback, for example.

At present, a water dynamics sensor usable for measuring water dynamics in a fine point of a plant such as a distal end of a new branch or a pedicel has not been developed. Development of a sensor has been desired that is usable for measuring water dynamics in a fine point such as a distal end of a new branch with high accuracy without causing a trouble on the fine point.

In view of the aforementioned circumstances, this invention is intended to provide a plant water dynamics sensor usable by anyone for measuring the dynamics of water (liquid) (water dynamics) flowing in a fine point of a plant such as a distal end of a new branch or a pedicel without causing damage (failure) of the plant.

Means of Solving Problem

A plant water dynamics sensor according to a first invention is used for measuring water dynamics in a plant, comprising: at least one heater-equipped temperature probe including a temperature sensor and a heater; at least one temperature probe including a temperature sensor; at least one electrical resistance probe including an electrical resistance measurement electrode; and a support that supports the heater-equipped temperature probe, the temperature probe, and the electrical resistance probe while the heater-equipped temperature probe, the temperature probe, and the electrical resistance probe are aligned parallel to each other.

A plant water dynamics sensor according to a second invention is characterized in that, in the first invention, the electrical resistance measurement electrode is arranged at a different level from the temperature sensors in a direction of sticking into the plant, and while the electrical resistance measurement electrode is arranged in a position at a xylem in the plant, each of the temperature sensors is arranged in a position at a phloem in the plant.

A plant water dynamics sensor according to a third invention is characterized in that, in the first invention, the temperature sensors and the electrical resistance measurement electrode are arranged at the same level in a direction of sticking into the plant.

A plant water dynamics sensor according to a fourth invention is characterized in that, in the first, second, or third invention, the at least one electrical resistance probe includes two electrical resistance probes.

A plant water dynamics sensor according to a fifth invention is characterized in that, in the first, second, third, or fourth invention, the at least one temperature probe includes two temperature probes, and the two temperature probes are provided in positions where the two temperature probes hold the heater-equipped temperature probe therebetween.

A plant water dynamics sensor according to a sixth invention is characterized in that, in the first, second, third, fourth, or fifth invention, the electrical resistance probe is formed as a probe integrated with the heater-equipped temperature probe or the temperature probe.

A plant water dynamics sensor according to a seventh invention is characterized in that, in the first, second, third, fourth, fifth, or sixth invention, the plant water dynamics sensor comprises at least one trapping probe including a flow channel into which sap in the plant is to flow.

A plant water dynamics sensor according to an eighth invention is characterized in that, in the seventh invention, the trapping probe is formed as a probe integrated with the heater-equipped temperature probe, the temperature probe, or the electrical resistance probe.

A plant water dynamics sensor according to a ninth invention is characterized in that, in the first, second, third, fourth, fifth, sixth, seventh, or eighth invention, the heater-equipped temperature probe, the temperature probe, the electrical resistance probe, and the support are formed of an SOI substrate, and each of the heater-equipped temperature probe, the temperature probe, and the electrical resistance probe is formed in a cantilever shape at an edge of the support.

Advantageous Effects of Invention

According to the first invention, the position of a xylem can be detected based on an electrical resistance measured at the electrical resistance probe. Thus, each of the temperature sensors can be arranged correctly in a position at a phloem or at the xylem. This facilitates attachment of the plant water dynamics sensor and water dynamics in the plant can be measured with high accuracy.

According to the second invention, by sticking each of the probes to a depth in the plant at which the xylem is detected by the electrical resistance probe, each of the temperature sensors can be arranged correctly in a position at the phloem. This facilitates attachment of the plant water dynamics sensor and a phloem flow can be measured with high accuracy in terms of its flow rate, and the like.

According to the third invention, by sticking each of the probes to a depth in the plant at which the xylem is detected by the electrical resistance probe, each of the temperature sensors can be arranged correctly in a position at the xylem. This facilitates attachment of the plant water dynamics sensor and a xylem flow can be measured with high accuracy in terms of its flow rate, and the like.

According to the fourth invention, by sticking each of the probes to a depth in the plant at which the xylem is detected by the two electrical resistance probes, the temperature sensors can be aligned along the phloem or the xylem.

According to the fifth invention, the direction of a sap flow can be specified by comparing temperatures measured at the two temperature probes.

According to the sixth invention, the number of probes can be reduced. This can reduce the size of the plant water dynamics sensor. The small number of probes can alleviate damage of the plant further.

According to the seventh invention, sap can be trapped using the trapping probe, so that the plant water dynamics sensor is usable for analyzing a nutritive substance in the sap.

According to the eighth invention, the number of probes can be reduced. This can reduce the size of the plant water dynamics sensor. The small number of probes can alleviate damage of the plant further.

According to the ninth invention, the size of the plant water dynamics sensor can be reduced, so that each of the probes can be formed into a minute size. Thus, even if this plant water dynamics sensor is installed on the plant, damage (failure) of the plant can be alleviated. Thus, the plant water dynamics sensor can be installed for a long time. As a result, water dynamics in the plant can be monitored for a long period of time, so that the plant can be supplied with water or replenished with nutrients (fertilized) appropriately in a manner that conforms to the growing status of the plant.

BRIEF DESCRIPTION OF DRAWINGS

FIG. 1 is a plan view of a plant water dynamics sensor according to a first embodiment;

FIG. 2 is a side view of the plant water dynamics sensor;

FIG. 17 is an explanatory view of an experimental device for experiment of position detection;

FIG. 18 is a graph showing a relationship between a sticking depth of a needle-like electrode and an electrical resistance;

FIG. 19 is a schematic view of an artificial plant experimental system used in experiment;

FIG. 21 is a graph showing a relationship between a flow rate and a K value;

FIG. 23 is a plan view of a trapping probe according to still another embodiment, which is formed as a single probe including a temperature sensor and a heater of a heater-equipped temperature probe; and FIG. 24 is a plan view of a trapping probe according to still further embodiment, which is formed as a single probe including an electrical resistance measurement electrode of an electrical resistance probe.

EMBODIMENTS FOR CARRYING OUT INVENTION

Figure 3:
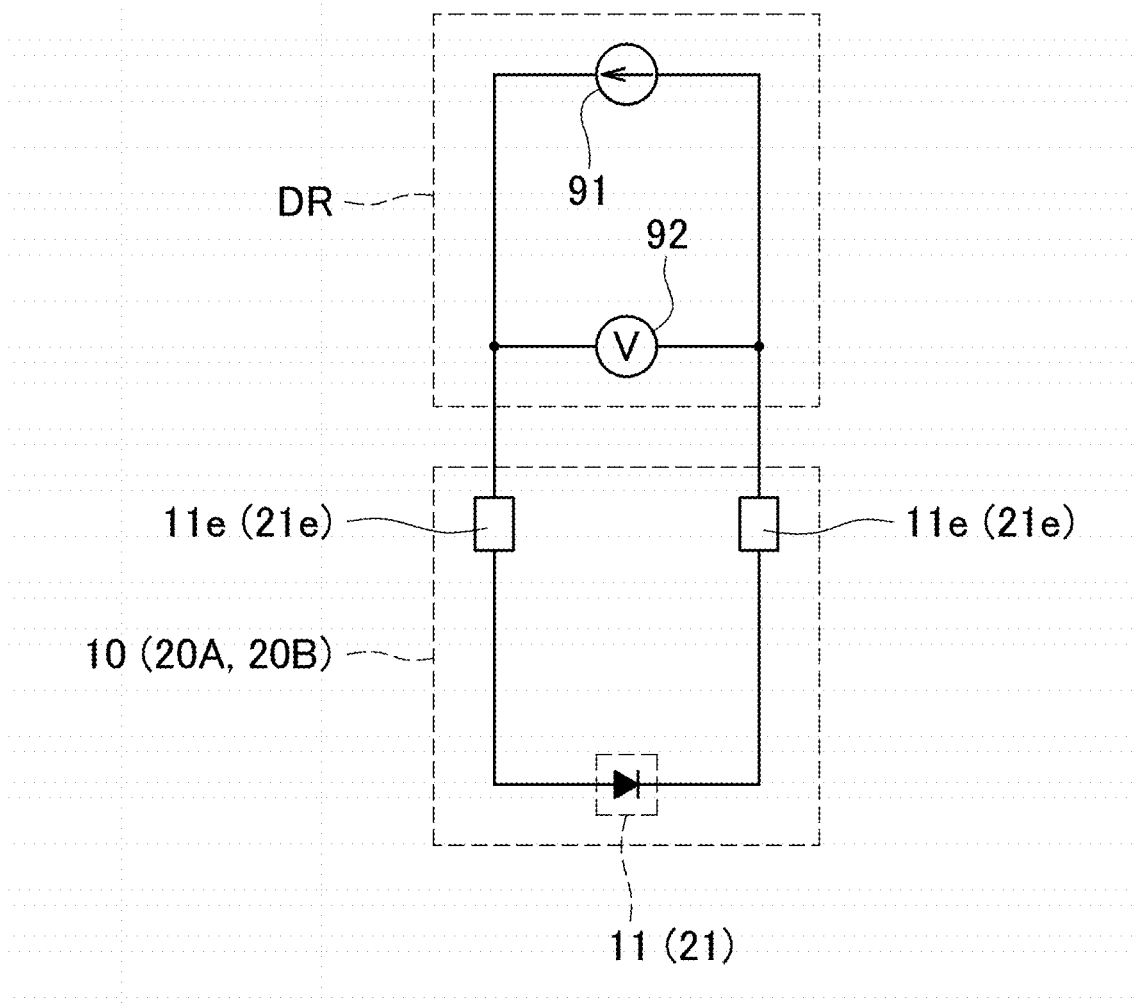
FIG. 3 is a circuit diagram including a temperature sensor of the plant water dynamics sensor.

Embodiments of this invention are described next based on the drawings.

A plant water dynamics sensor according to this invention is used for measuring water dynamics in a plant. The plant water dynamics sensor can be attached easily to a fine point of a plant such as a distal end of a new branch (hereinafter simply called a new branch distal end) or a pedicel of the plant and is usable for measuring water dynamics in such a fine point.

The plant water dynamics sensor according to this invention is used for measuring water dynamics in a plant using the Granier method. The principle of the Granier method is described briefly before description of the plant water dynamics sensor according to this invention.

The Granier method is to calculate a sap flow rate F using a Granier sensor. The Granier sensor includes rod-shaped probes in a pair. These probes in a pair each include a temperature sensor. One of the probes in a pair includes a heater (hereinafter simply called a heater-equipped temperature probe HP). The other probe is used for reference and simply called a temperature probe RP.

A method of installing the Granier sensor on a tree and measuring the sap flow rate F in the tree is described below.

First, holes are formed in two places of the trunk of the tree with a drill, for example. The heater-equipped temperature probe HP and the temperature probe RP of the Granier sensor are inserted in the corresponding holes to be installed on the tree and left at rest for one day or more. The temperature probe RP and the heater-equipped temperature probe HP of the Granier sensor are aligned in this order along a sap flow in a direction from an upstream side toward a downstream side. Specifically, if sap flows in a direction from a root toward a distal end, the temperature probe RP is inserted in a hole closer to the root and the heater-equipped temperature probe HP is inserted in a hole closer to the distal end.

Next, the heater of the heater-equipped temperature probe HP of the Granier sensor is actuated. This generates temperature difference $\Delta T$ between the respective temperature sensors of the probes HP and RP in a pair. As shown by the following formula 1, the temperature difference $\Delta T$ is used as a function of a sap flow speed u. By using this function, the sap flow speed u can be calculated based on the temperature difference $\Delta T$.

$$u = \frac{1}{\alpha}\left\{\frac{\Delta T(0) - \Delta T(u)}{\Delta T(u)}\right\}^{\frac{1}{\beta}} = \frac{1}{\alpha}K^{\frac{1}{\beta}} \qquad \text{[Formula 1]}$$

In this formula, u is an average sap flow speed [m/s], $\Delta T(u)$ is temperature difference [° C.] between the heater-equipped temperature probe HP and the temperature probe RP if an average sap flow speed is u, $\Delta T(0)$ is a maximum temperature [° C.] of $\Delta T$, and $\alpha$ and $\beta$ are coefficients obtained from observed data.

Based on the following formula 2, the sap flow rate F can be calculated using the sap flow speed u.

$$F = u \times S \qquad \text{[Formula 2]}$$

In this formula, F is a sap flow rate [m³/s] and S is a cross-sectional area [m²] formed by the probes HP and RP in a peripheral direction of a trunk.

If the flow rate F of sap flowing in a tree is high (if the sap flow speed u is high), for example, the temperature difference $\Delta T$ between the respective temperature sensors of the probes HP and RP in a pair of the Granier sensor is small. This is because, while the heater applies constant heat to the heater-equipped temperature probe HP, this heat is carried away by a large quantity of sap flowing in the vicinity of the heater-equipped temperature probe HP. If the sap flow rate F is low (if the sap flow speed u is low), the temperature difference $\Delta T$ between the respective temperature sensors of the probes HP and RP in a pair of the Granier sensor is large. This is because, while the heater applies constant heat to the heater-equipped temperature probe HP, this heat supplied to the heater-equipped temperature probe HP stays without being carried away by sap as the sap flows in small quantity in the vicinity of the heater-equipped temperature probe HP.

>First Embodiment>

A plant water dynamics sensor 1 according to a first embodiment of this invention is described next.

The plant water dynamics sensor 1 according to this embodiment is suitably used particularly for measuring the direction and the flow rate (flow speed) of a phloem flow.

As shown in FIGS. 1 and 2, the plant water dynamics sensor 1 includes one heater-equipped temperature probe 10, temperature probes 20A and 20B in a pair, electrical resistance probes 30A and 30B in a pair, and a support 80. While all the probes 10, 20A, 20B, 30A, and 30B are aligned parallel to each other in the same horizontal plane, each of these probes 10, 20A, 20B, 30A, and 30B is supported on the support 80 at its base end. By sticking these probes 10, 20A, 20B, 30A, and 30B into a plant, the plant water dynamics sensor 1 is installed on the plant.

The probes 10, 20A, 20B, 30A, and 30B, and the support 80 are formed by processing an SOI substrate using MEMS technology involving thin film formation by means of photolithography, etching, sputtering process, or vacuum deposition process, for example.

The SOI substrate has a three-layer structure including a support substrate SB, an active layer AL, and an oxide film layer BL caught between the support substrate SB and the active layer AL. The support substrate SB is made of silicon (Si) and has a thickness from 400 to 500 µm. The active layer AL is made of silicon (Si) and has a thickness of about 10 µm. The oxide film layer BL is made of silicon dioxide ($SiO_2$) and has a thickness from 0.1 to 1 µm. The active layer AL has heat conductivity. The oxide film layer BL is an insulator that lets little heat and electricity pass through.

(Support)

The support 80 is a member that supports the probes 10, 20A, 20B, 30A, and 30B. The support 80 is a plate member rectangular in a plan view. All the probes 10, 20A, 20B, 30A, and 30B are supported on one long side part of the support 80. The support 80 has such a length in its long side direction as is required only to allow all the probes 10, 20A, 20B, 30A, and 30B to be aligned at intervals of an inter-axial distance W described later. The length of the support 80 in its short side direction is not particularly limited.

If the inter-axial distance W between adjacent ones of the probes 10, 20A, 20B, 30A, and 30B is about 2 mm, for example, the support 80 can be formed in such a manner that the length in its long side direction is about 12 mm and the length in its short side direction is about 8 mm. The support 80 has the same thickness as the SOI substrate. Specifically, the support 80 is formed in such a manner that one side thereof has a length of about several millimeters in a plan view and the thickness thereof does not exceed 1 mm.

(Probe)

Each of the probes 10, 20A, 20B, 30A, and 30B is a rod-shaped member made of a thin plate and is formed in a cantilever shape at an edge (long side part) of the support 80. Each of the probes 10, 20A, 20B, 30A, and 30B is formed of the active layer AL, the oxide film layer BL, and an upper part of the support substrate SB. Specifically, each of the probes 10, 20A, 20B, 30A, and 30B is formed by removing a lower part of the support substrate SB into a thickness smaller than that of the SOI substrate. The thickness of each of the probes 10, 20A, 20B, 30A, and 30B is not particularly limited and is set to be from 40 to 200 µm, for example. A thickness not falling below 40 µm achieves sufficient strength, so that the probes 10, 20A, 20B, 30A, and 30B are free from the risk of being bent during insertion and extraction into and from a plant. Further, a xylem XY and a phloem PH have diameters from about 100 to 200 µm, while these diameters depend on the type of a plant. Thus, with a thickness not exceeding 200 µm, even if the probes 10, 20A, 20B, 30A, and 30B are stuck into the xylem XY or the phloem PH, the xylem XY or the phloem PH can be prevented from being blocked by these probes.

Each of the probes 10, 20A, 20B, 30A, and 30B is formed into a dimension that allows each of the probes 10, 20A, 20B, 30A, and 30B to be stuck into a fine point of a plant such as a new branch distal end or a pedicel having a stem diameter or an axis diameter of about several millimeters and to be arranged in this fine point. More specifically, all the probes 10, 20A, 20B, 30A, and 30B are formed into lengths (lengths in their axis directions from their base ends to their tips) and widths that allow respective tip portions of these probes to be arranged in the xylem XY and/or the phloem PH at the fine point of the plant while these probes are stuck into this fine point of the plant and installed on this fine point (lengths are from 50 µm to 1 mm, for example, and widths are from 50 to 300 µm, for example).

The tip portion of each of the probes 10, 20A, 20B, 30A, and 30B is preferably formed into a pointed shape such as a triangular shape. Forming the tip portion of each of the probes 10, 20A, 20B, 30A, and 30B into a pointed shape can reduce insertion resistance occurring when the probes 10, 20A, 20B, 30A, and 30B are inserted into a fine point of a plant. Specifically, the probes 10, 20A, 20B, 30A, and 30B can be stuck into and installed on the fine point of the plant smoothly. This can prevent such as breakage of the tip portions of the probes 10, 20A, 20B, 30A, and 30B that is to occur when the probes 10, 20A, 20B, 30A, and 30B are stuck into the fine point of the plant.

(Heater-Equipped Temperature Probe)

The heater-equipped temperature probe 10 includes a temperature sensor 11 and a heater 12. Regarding the dimension of the heater-equipped temperature probe 10, a length is 300 µm and a width is 200 µm, for example.

The temperature sensor 11 has the function of sensing a temperature. As long as the temperature sensor 11 can be provided at the tip portion of the heater-equipped temperature probe 10 of the aforementioned dimension, the size of the temperature sensor 11 is not particularly limited. For example, a sensor made of a pn-junction diode formed using an oxidation and diffusion furnace is applicable as the temperature sensor 11.

The heater 12 can function to supply heat to the heater-equipped temperature probe 10. As long as the heater 12 can be provided at the heater-equipped temperature probe 10 of the aforementioned dimension, the size of the heater 12 is not particularly limited. For example, a heater made of a pn-junction diode formed using an oxidation and diffusion furnace is applicable as the heater 12. The heater 12 is not always required to be provided at the tip portion of the heater-equipped temperature probe 10 but can be provided in any position where the heater 12 can supply heat to the heater-equipped temperature probe 10.

(Temperature Probe)

The temperature probes 20A and 20B in a pair each include a temperature sensor 21. Each of the temperature probes 20A and 20B may have the same dimension as the heater-equipped temperature probe 10. For example, the length and the width of each of the temperature probes 20A and 20B are 300 µm and 200 µm respectively. The sensor used as the temperature sensor 11 of the heater-equipped temperature probe 10 is also applicable as the temperature sensor 21.

The plant water dynamics sensor 1 includes the two temperature probes 20A and 20B. These two temperature probes 20A and 20B are provided in positions where the temperature probes 20A and 20B hold the heater-equipped temperature probe 10 therebetween. Specifically, the temperature probe 20A, the heater-equipped temperature probe 10, and the temperature probe 20B are aligned in this order.

(Electrical Resistance Probe)

The electrical resistance probes 30A and 30B in a pair each include electrical resistance measurement electrodes 33 and 33 in a pair. Regarding the dimension of each of the electrical resistance probes 30A and 30B, each of these probes is formed into a length larger than that of each of the heater-equipped temperature probe 10 and the temperature probes 20A and 20B. For example, the length and the width of each of the electrical resistance probes 30A and 30B is 400 µm and 200 µm respectively.

The electrical resistance measurement electrodes 33 and 33 in a pair are electrodes used for measuring the electrical resistance of a substance such as phloem sap or xylem sap in a plant existing between these electrical resistance measurement electrodes 33 and 33. As long as the electrical resistance measurement electrodes 33 and 33 can be provided at the tip portion of each of the electrical resistance probes 30A and 30B of the aforementioned dimension, the size of the electrical resistance measurement electrodes 33 and 33 is not particularly limited. For example, an aluminum (Al) thin plate is applicable as the electrical resistance measurement electrode 33.

As described above, each of the electrical resistance probes 30A and 30B is formed into a length larger than that of each of the heater-equipped temperature probe 10 and the temperature probes 20A and 20B. More specifically, each of the electrical resistance probes 30A and 30B is formed into a length larger than that of each of the heater-equipped temperature probe 10 and the temperature probes 20A and 20B by a distance between the center of the phloem PH and the center of the xylem XY in a plant as a measurement target. This difference in length depends on the type of a plant as a measurement target or the diameter of a stem of the plant and is set to be from 50 to 300 µm, for example.

Each of the electrical resistance probes 30A and 30B is formed into a length larger than that of each of the heater-equipped temperature probe 10 and the temperature probes 20A and 20B. The electrical resistance measurement electrode 33 is provided at the tip portion of each of the electrical resistance probes 30A and 30B. The temperature sensor 11 is provided at the tip portion of the heater-equipped temperature probe 10. The temperature sensor 21 is provided at the tip portion of each of the temperature probes 20A and 20B. In this way, a level in a direction of sticking into a plant as a measurement target (the axis direction of each of the probes 10, 20A, 20B, 30A, and 30B) differs by a distance D between the electrical resistance measurement electrode 33 and each of the temperature sensors 11 and 21. The electrical resistance measurement electrode 33 is arranged in such a way as to be arranged in a position at a greater distance from the respective base ends of the probes 10, 20A, 20B, 30A, and 30B than the temperature sensors 11 and 21 to reach a deeper position inside a plant.

As described above, by providing the distance D between the electrical resistance measurement electrode 33 and each of the temperature sensors 11 and 21, while the probes 10, 20A, 20B, 30A, and 30B are stuck into a plant and the electrical resistance measurement electrode 33 is arranged in a position at the xylem XY in the plant, each of the temperature sensors 11 and 21 is arranged in a position at the phloem PH in the plant. In other words, the distance D between the electrical resistance measurement electrode 33 and each of the temperature sensors 11 and 21 is set in such a manner that, while the electrical resistance measurement electrode 33 is arranged in a position at the xylem XY in the plant, each of the temperature sensors 11 and 21 is arranged in a position at the phloem PH in the plant. The distance D depends on the type of a plant as a measurement target or the diameter of a stem of the plant and is set to be from 50 to 300 µm, for example.

The plant water dynamics sensor 1 includes the two electrical resistance probes 30A and 30B. These two electrical resistance probes 30A and 30B are provided in positions where the electrical resistance probes 30A and 30B hold the heater-equipped temperature probe 10 and the temperature probes 20A and 20B therebetween. Specifically, the electrical resistance probe 30A, the temperature probe 20A, the heater-equipped temperature probe 10, the temperature probe 20B, and the electrical resistance probe 30B are aligned in this order.

(Data Logger)

The temperature sensors 11 and 21, the heater 12, and the electrical resistance measurement electrode 33 of the plant water dynamics sensor 1 are connected to a data logger DR for power supply and collection of data of various types.

The active layer AL forming each of the probes 10, 20A, 20B, 30A, and 30B is continuous with the active layer AL forming the support 80 to become an integrated layer. In the support 80, the active layer AL connected to each of the probes 10, 20A, 20B, 30A, and 30B is removed in a part between adjacent ones of the probes 10, 20A, 20B, 30A, and 30B. Thus, the oxide film layer BL having thermally and electrically insulating properties is interposed in this part. Specifically, the respective active layers AL of all the probes 10, 20A, 20B, 30A, and 30B are thermally and electrically dependent of each other by the presence of the oxide film layer BL.

Electrode pads 11e, 21e, 12e, and 33e are provided on the active layer AL of the support 80 and are connected to the temperature sensor 11 and 21, the heater 12, and to the electrical resistance measurement electrode 33 respectively.

More specifically, the electrode pads 11e and 11e in a pair for the temperature sensor 11, and the electrode pads 12e and 12e in a pair for the heater 12 are provided on the active layer AL of the support 80 integrated with the active layer AL forming the heater-equipped temperature probe 10. The temperature sensor 11 has an anode and a cathode (those of a pn-junction diode forming the temperature sensor 11) connected to corresponding ones of the electrode pads 11e via interconnect lines. Further, the heater 12 has an anode and a cathode (those of a pn-junction diode forming the heater 12) connected to corresponding ones of the electrode pads 12e via interconnect lines.

The electrode pads 21e and 21e in a pair for the temperature sensor 21 are provided on the active layer AL of the support 80 integrated with the active layer AL forming each of the temperature probes 20A and 20B. The temperature sensor 21 has an anode and a cathode (those of a pn-junction diode forming the temperature sensor 21) connected to corresponding ones of the electrode pads 21e via interconnect lines.

The electrode pads 33e and 33e in a pair for corresponding ones of the electrical resistance measurement electrodes 33 and 33 are provided on the active layer AL of the support 80 integrated with the active layer AL forming each of the electrical resistance probes 30A and 30B. The electrical resistance measurement electrodes 33 and 33 in a pair are connected to corresponding ones of the electrode pads 33e via interconnect lines.

The electrode pads 11e, 12e, 21e, and 33e, and the interconnect lines are formed together with the electrical resistance measurement electrode 33 by the following method, for example. First, an insulating film ($SiO_2$) is formed on the active layer AL using an oxidation furnace. Then, the electrical resistance measurement electrode 33, the electrode pads 11e, 12e, 21e, and 33e, and the interconnect lines are formed using photofabrication technique. At this time, contacts necessary for conduction with the temperature sensor 11 and 21 and the heater 12 are also formed.

As shown in FIG. 3, the data logger DR includes a constant current source 91 and a voltmeter 92. The constant current source 91 is connected between the electrode pads 11e and 11e (21e and 21e) and supplies a constant current in a forward direction to the temperature sensor 11 (21 ) as a pn-junction diode. The voltmeter 92 is connected between the electrode pads 11e and 11e (21e and 21e) and measures a voltage between the anode and the cathode of the temperature sensor 11 (21) as a pn-junction diode.

The forward characteristics of a diode change with temperature. This temperature change is known to change a voltage in response to flow of a constant current in the diode. As described above, a temperature can be calculated by measuring a voltage of the temperature sensor 11 (21) using the voltmeter 92.

Figure 4:
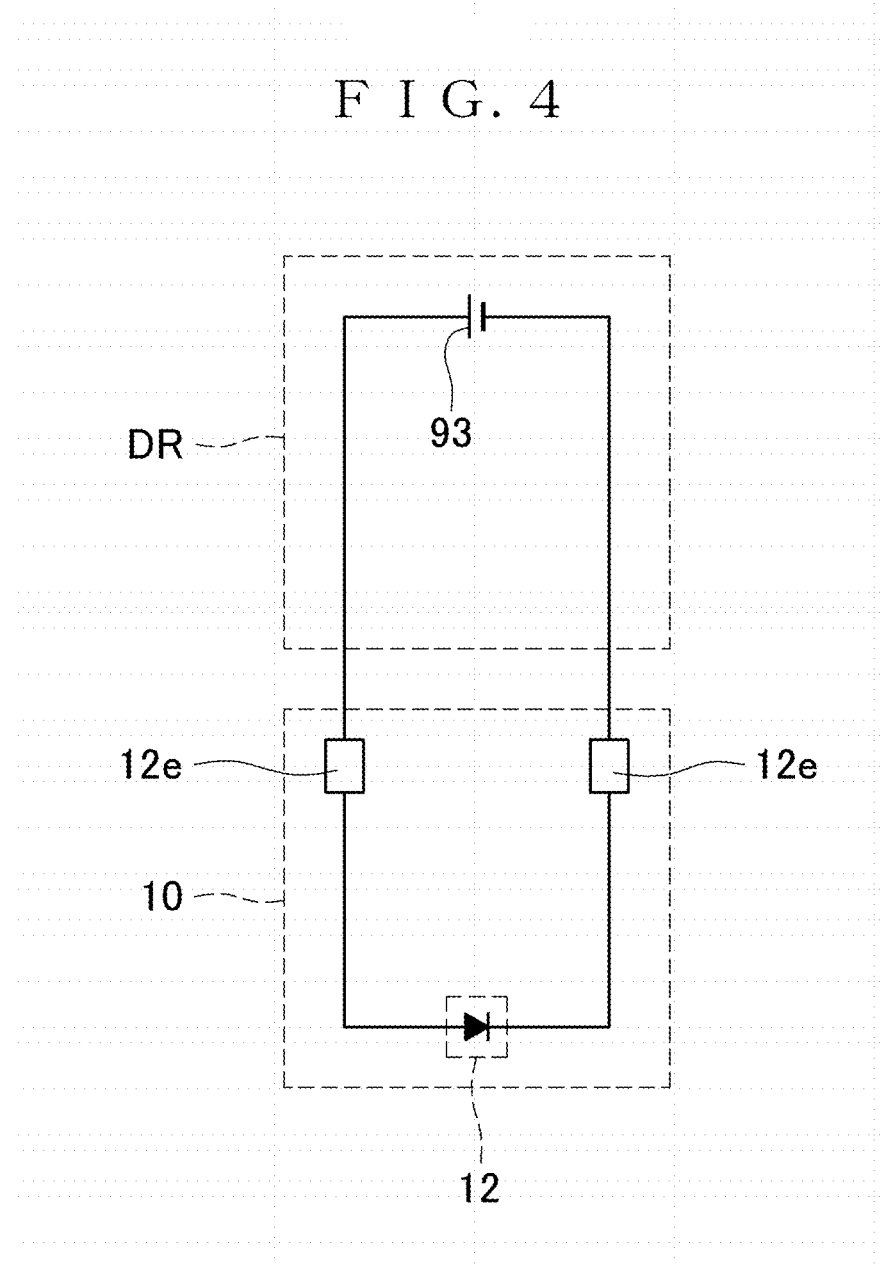
FIG. 4 is a circuit diagram including a heater of the plant water dynamics sensor.

As shown in FIG. 4, the data logger DR includes a DC constant voltage source 93. The DC constant voltage source 93 is connected between the electrode pads 12e and 12e and supplies a constant voltage in a forward direction to the heater 12 as a pn-junction diode. Heat can be generated by flowing a current in the heater 12.

Figure 5:
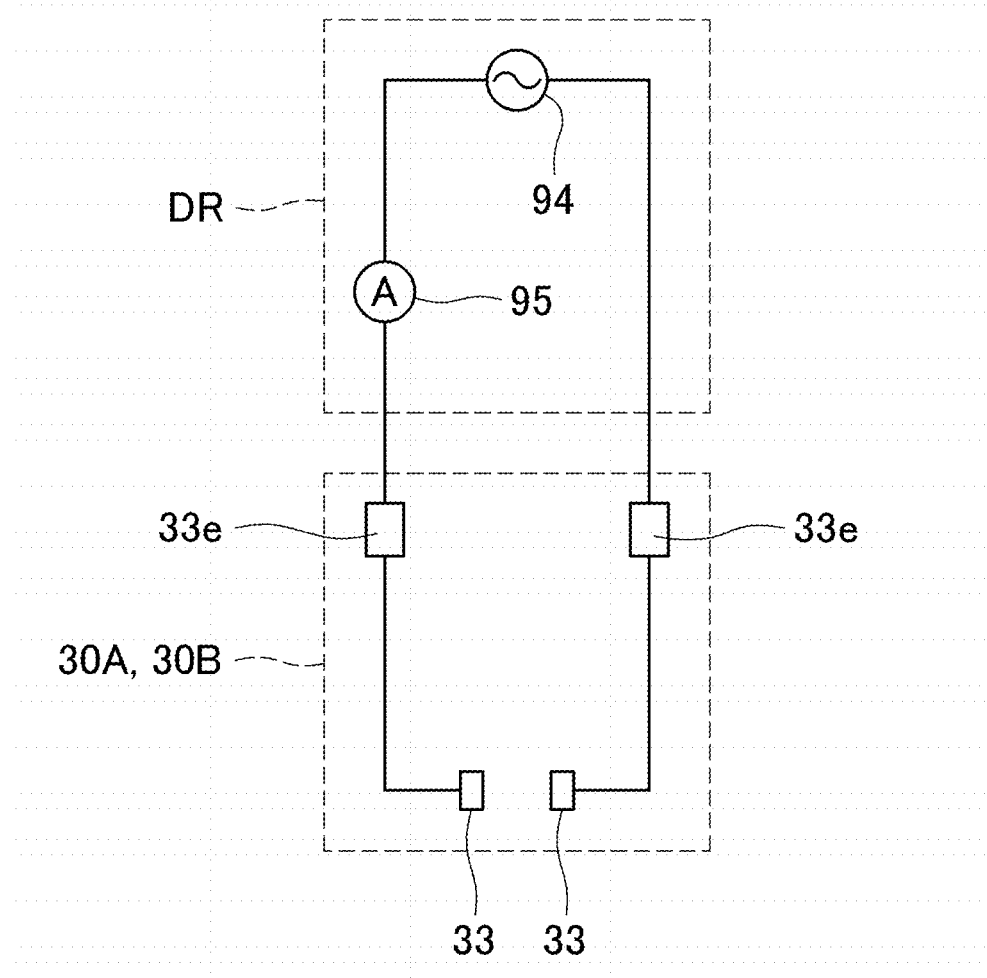
FIG. 5 is a circuit diagram including an electrical resistance measurement electrode of the plant water dynamics sensor.

As shown in FIG. 5, the data logger DR includes an AC source 94 and an ammeter 95. The AC source 94 and the ammeter 95 are connected in series between the electrode pads 33e and 33e. A current is supplied from the AC source 94 to between the electrical resistance measurement electrodes 33 and 33 in a pair. A current flowing between the electrical resistance measurement electrodes 33 and 33 in a pair is measured using the ammeter 95. According to Ohm's law, an electrical resistance between the electrical resistance measurement electrodes 33 and 33 in a pair can be calculated based on a current measured using the ammeter 95.

(Manufacturing Method)

As described above, the plant water dynamics sensor 1 is formed by processing an SOI substrate using MEMS technology. The following briefly describes a method of forming each of the probes 10, 20A, 20B, 30A, and 30B, and the support 80 using MEMS technology.

First, a pn-junction diode to become each of the temperature sensors 11 and 21 and the heater 12 is formed on the active layer AL of the SOI substrate using an oxidation and diffusion furnace. More specifically, a hole (p-type) for diffusion is formed on the active layer AL and then n-diffusion (n-type) is formed. Next, a contact of the pn-junction diode, the electrical resistance measurement electrode 33, the electrode pads 11e, 12e, 21e, and 33e, and the interconnect lines are formed. More specifically, an Al thin film is deposited on the active layer Al using sputtering process or deposition process. A resist is applied onto the Al thin film to form the contact, the electrical resistance measurement electrode 33, the electrode pads 11e, 12e, 21e, and 33e, and the interconnect lines.

A next step is photolithography into probe shapes on the front surface of the SOI substrate. Then, the front surface is etched to the oxide film layer BL using dry etching such as ICP-RIE, thereby forming prototypes of the probe shapes. Then, the back surface of the SOI substrate is partially etched back so as to form each of the probes 10, 20A, 20B, 30A, and 30B in a cantilever shape.

As long as the plant water dynamics sensor 1 can be formed into the aforementioned dimensions and can be formed to achieve the aforementioned functions, the plant water dynamics sensor 1 may be formed by a method other than MEMS technology. Further, a base material is not limited to an SOI substrate.

A method of measuring water dynamics in a plant using the plant water dynamics sensor 1 is described next.

(Method of Attachment)

First, the plant water dynamics sensor 1 is attached to a new branch distal end of a plant as a measurement target.

Figure 6:
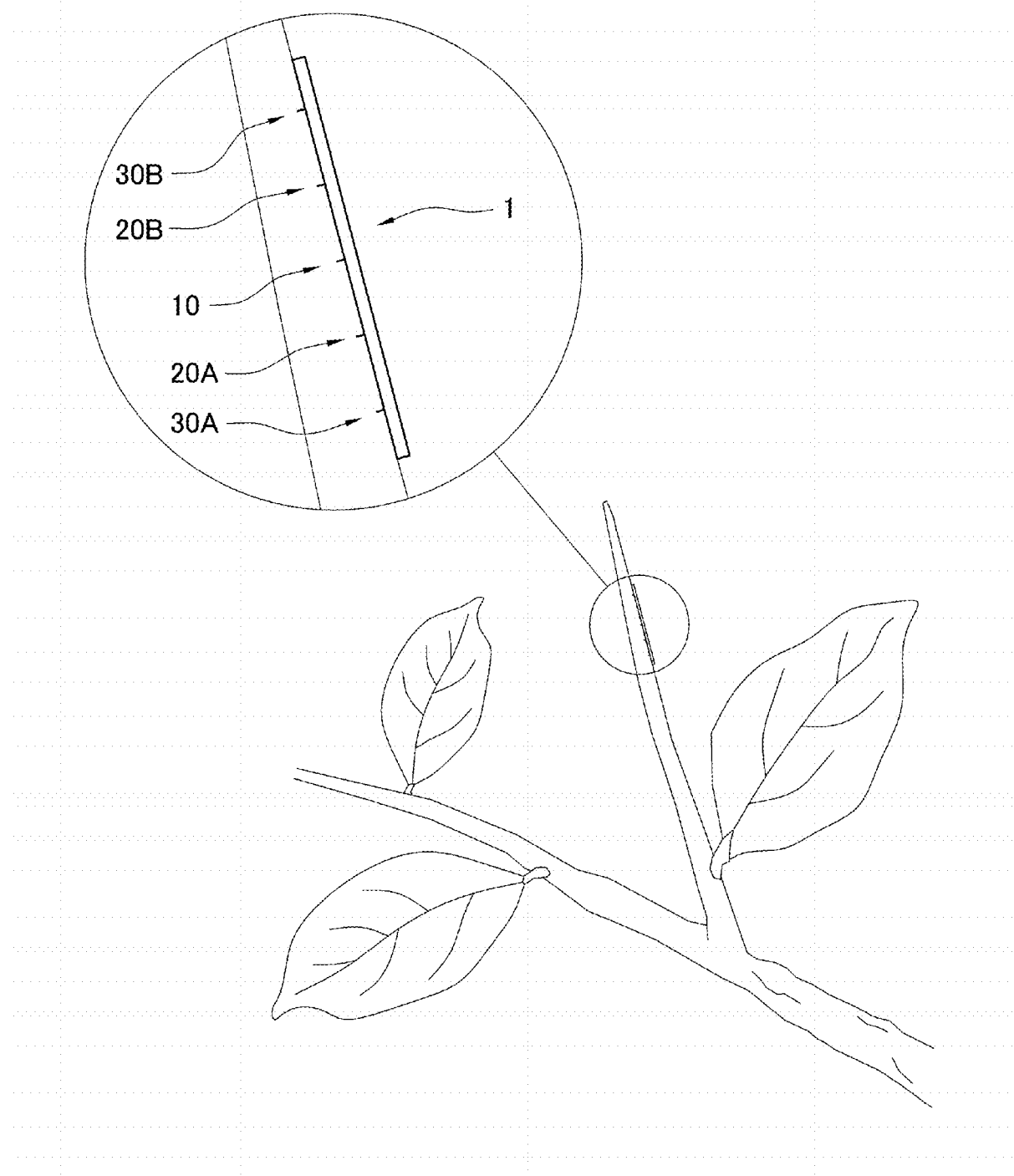
FIG. 6 is an explanatory view schematically showing usage of the plant water dynamics sensor.

More specifically, as shown in FIG. 6, all the probes 10, 20A, 20B, 30A, and 30B of the plant water dynamics sensor 1 are attached by being stuck into a fine point of the plant. At this time, like in the aforementioned Granier method, the probes 10, 20A, 20B, 30A, and 30B are aligned in the direction of a flow of water (liquid) in the fine point of the plant, specifically, along the xylem XY and the phloem PH. Which of the temperature probes 20A and 20B is to be arranged in a position closer to a distal end or closer to a root can be determined freely.

Figure 7:
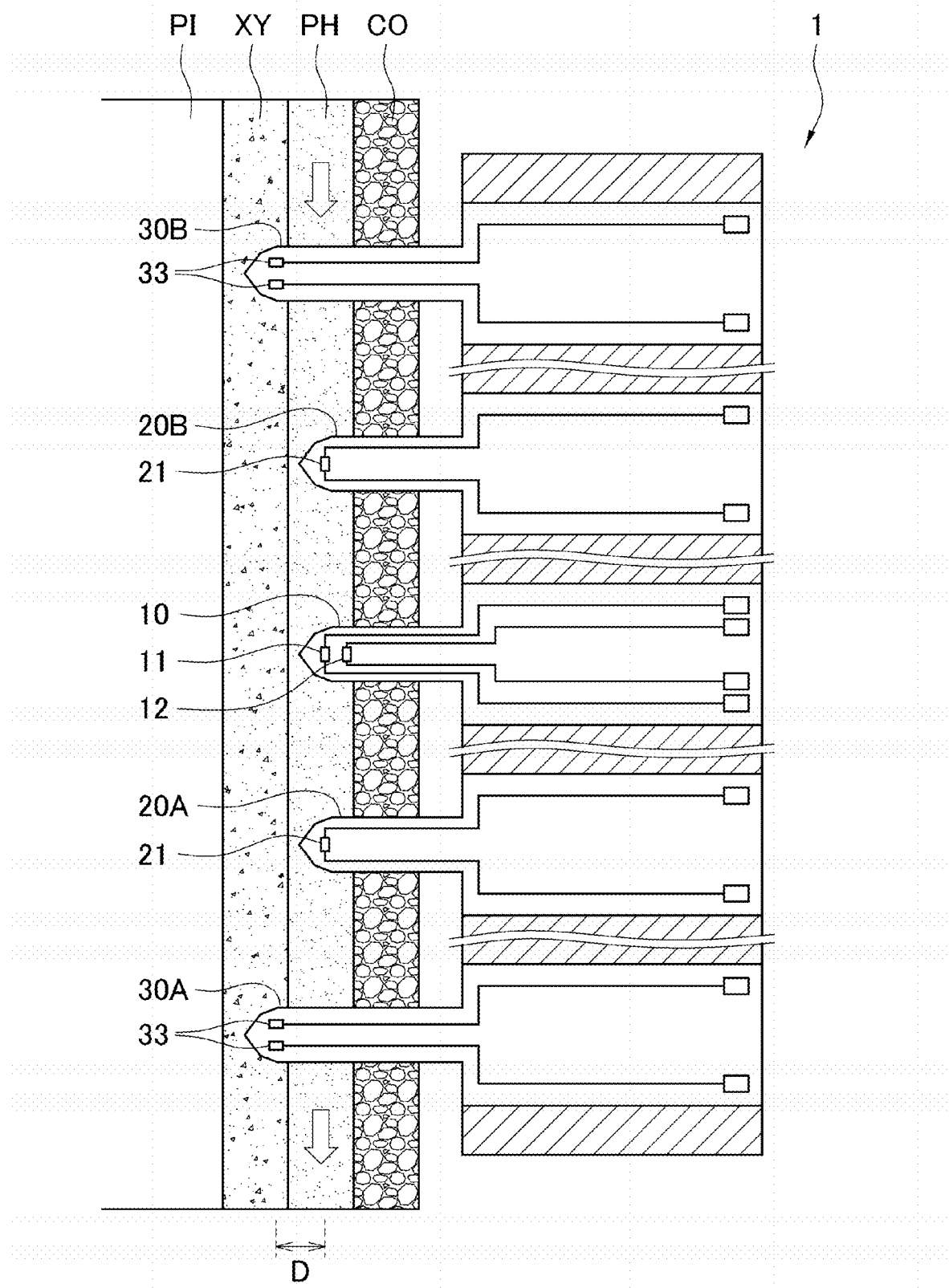
FIG. 7 is an explanatory view schematically showing usage of the plant water dynamics sensor in an enlarged manner.

As shown in FIG. 7, as the probes 10, 20A, 20B, 30A, and 30B are stuck into the fine point of the plant, the electrical resistance measurement electrode 33 provided to each of the electrical resistance probes 30A and 30B passes through a cortical layer CO and the phloem PH in the plant to reach the xylem XY. As the probes 10, 20A, 20B, 30A, and 30B are stuck more deeply, the electrical resistance measurement electrode 33 reaches a pith PI of the plant.

Xylem sap flowing in the xylem XY contains minerals, so that it has the property of being lower in electrical resistance than water in the other parts (including cortical layer CO, phloem PH, pith PI, and the like). By using this property, the electrical resistance measurement electrode 33 can be arranged in a position at the xylem XY by sticking each of the probes 10, 20A, 20B, 30A, and 30B to a depth at which an electrical resistance measured at each of the electrical resistance probes 30A and 30B is reduced.

Further, as described above, the electrical resistance measurement electrode 33 and each of the temperature sensors 11 and 21 are separated in a direction of sticking by the distance D. Thus, by arranging the electrical resistance measurement electrode 33 in a position at the xylem XY, each of the temperature sensors 11 and 21 can be arranged by itself in a position at the phloem PH in the plant.

As described above, the plant water dynamics sensor 1 can be installed on a plant only by sticking the probes 10, 20A, 20B, 30A, and 30B into the plant. Thus, the plant water dynamics sensor 1 does not require process of forming a hole in a stem with a drill for installation on the plant or process of forming a cut in the plant, and the like, unlike a conventional sensor used for measuring water dynamics in the plant. This facilitates attachment of the plant water dynamics sensor 1 to the plant.

The electrical resistance probes 30A and 30B have the function of detecting the position of the xylem XY. Based on an electrical resistance measured at each of the electrical resistance probes 30A and 30B, the position of the xylem XY can be detected. By sticking each of the probes 10, 20A, 20B, 30A, and 30B to a depth in a plant at which the xylem XY is detected by the electrical resistance probes 30A and 30B, each of the temperature sensors 11 and 21 can be arranged correctly in a position at the phloem PH. This eliminates the need of measuring a depth of sticking of each of the probes 10, 20A, 20B, 30A, and 30B into a plant using a specialized unit such as a micrometer, thereby facilitating attachment of the plant water dynamics sensor 1. As a result, water dynamics in a plant described later (in this embodiment, the flow rate of a phloem flow, for example) can be measured with high accuracy.

Only one electrical resistance probe 30 may be provided. However, like in the plant water dynamics sensor 1 of this embodiment, providing the two electrical resistance probes 30A and 30B is more preferable. This is because, by sticking each of the probes 10, 20A, 20B, 30A, and 30B to a depth in a plant at which the two electrical resistance probes 30A and 30B detect the xylem XY simultaneously, the temperature sensors 11 and 21 can be aligned along the phloem PH.

In particular, like in this embodiment, by providing the two electrical resistance probes 30A and 30B in positions where the electrical resistance probes 30A and 30B hold the heater-equipped temperature probe 10 and the temperature probes 20A and 20B therebetween, specifically, in positions external to the heater-equipped temperature probe 10 and the temperature probes 20A and 20B, a distance between the two electrical resistance probes 30A and 30B is increased. Thus, the temperature sensors 11 and 21 can be aligned more correctly along the phloem PH.

(Measuring Method)

Next, water dynamics in the plant is measured using the plant water dynamics sensor 1 attached to the plant.

First, the heater 12 of the heater-equipped temperature probe 10 is actuated. By actuating the heater 12, heat energy from the heater 12 is supplied to the heater-equipped temperature probe 10. The heat energy supplied to the heater-equipped temperature probe 10 is emitted from a surface of the heater-equipped temperature probe 10 to phloem sap flowing in the phloem PH.

At this time, the temperature of the heater-equipped temperature probe 10 and those of the temperature probes 20A and 20B can be measured using the temperature sensors 11 and 21 respectively. The direction of a phloem flow can be specified by comparing temperatures measured at the two temperature probes 20A and 20B for the following reason.

The two temperature probes 20A and 20B are provided in positions where the temperature probes 20A and 20B hold the heater-equipped temperature probe 10 therebetween. Thus, if phloem sap flows from a distal end toward a root of the plant (in a direction indicated by hollow arrows of FIG. 7), the temperature probe 20A closer to the root is warmed by the phloem sap increased in temperature by the heater-equipped temperature probe 10 to be placed at a higher temperature than the temperature probe 20B closer to the distal end.

Conversely, if phloem sap flows from the root toward the distal end of the plant, the temperature probe 20B closer to the distal end is warmed by the phloem sap increased in temperature by the heater-equipped temperature probe 10. Thus, a temperature detected at the temperature probe 20B is higher than that detected at the temperature probe 20A closer to the root.

Specifically, the direction of a phloem flow can be determined to be from the temperature probe 20B (20A) at a lower temperature toward the temperature probe 20A (20B) at a higher temperature.

A xylem flow is generally from a root toward a distal end of a plant. By contrast, the direction of a phloem flow cannot be grasped from the outer shape of a plant. Meanwhile, the direction of a phloem flow can be determined using the plant water dynamics sensor 1.

Next, based on the temperatures measured at the heater-equipped temperature probe 10 and the temperature probes 20A and 20B, the flow rate (flow speed) of the phloem flow in the new branch distal end is measured according to the aforementioned Granier method. Here, the flow rate (flow speed) is calculated based on a temperature difference between the temperature probe 20B (20A) at a lower temperature out of the two temperature probes 20A and 20B and the heater-equipped temperature probe 10. This is because the temperature probe 20B (20A) at a lower temperature is arranged on an upstream side of the phloem flow relative to the heater-equipped temperature probe 10.

If the flow rate of the phloem flow is high (if the flow speed thereof is high), for example, phloem sap in the vicinity of the heater-equipped temperature probe 10 is always replaced by new phloem sap. Thus, if constant heat energy is supplied to the heater-equipped temperature probe 10, the temperature of the heater-equipped temperature probe 10 is taken away by phloem sap in the vicinity of the heater-equipped temperature probe 10. By contrast, if the flow rate of the phloem flow is low (if the flow speed thereof is low), phloem sap stays in a place in the vicinity of the heater-equipped temperature probe 10. Thus, if constant heat energy is supplied to the heater-equipped temperature probe 10, the temperature of the heater-equipped temperature probe 10 is accumulated.

In this way, the flow speed and the flow rate of the phloem flow can be calculated by measuring the temperature difference $\Delta T$ between the heater-equipped temperature probe 10 and the temperature probe 20B (20A).

Heat energy supplied from the heater 12 to the heater-equipped temperature probe 10 is not supplied to the temperature probes 20A and 20B. This is because supply of the heat energy from the heater 12 to the temperature probes 20A and 20B next to the heater 12 is blocked by the presence of the oxide film layer BL.

The plant water dynamics sensor 1 is formed of the SOI substrate. This can reduce the size of the plant water dynamics sensor 1, so that each of the probes 10, 20A, 20B, 30A, and 30B can be formed into a minute size. Thus, even if the plant water dynamics sensor 1 is installed on a plant, damage (failure) of the plant can be alleviated. Thus, the plant water dynamics sensor 1 can be installed for a long time. As a result, water dynamics in the plant can be monitored for a long period of time, so that the plant can be supplied with water or replenished with nutrients (fertilized) appropriately in a manner that conforms to the growing status of the plant.

Further, each of the probes 10, 20A, 20B, 30A, and 30B is formed into a minute size. Thus, even if the probes 10, 20A, 20B, 30A, and 30B are installed on a plant by being stuck into the plant, stress on the plant can be alleviated. In other words, change in water dynamics in a place of the plant where the probes 10, 20A, 20B, 30A, and 30B are installed can be reduced between before the installation and after the installation. This makes it possible to measure the dynamics of water (liquid) flowing in the place of the installation immediately after the probes 10, 20A, 20B, 30A, and 30B are installed on the plant. Additionally, while a conventional sensor are hard to install on a fine point of a plant such as a new branch distal end or a pedicel, the probes 10, 20A, 20B, 30A, and 30B can be attached to such a fine point easily.

The heater-equipped temperature probe 10 and the temperature probes 20A and 20B are formed in such a manner that, while the probes 10, 20A, and 20B are attached to a fine point of a plant, the inter-axial distance W can be set at a distance that allows measurement of the flow rate (flow speed) of water (liquid) flowing in this fine point. More specifically, this can be achieved by setting the inter-axial distance W between corresponding ones of the probes 10, 20A, and 20B to be from 1 to 20 mm.

If the inter-axial distance W is smaller than 1 mm, heat energy from the heater 12 might be supplied to the temperature probes 20A and 20B via tissues of a plant, for example. Meanwhile, if the inter-axial distance W is larger than 20 mm, it might be impossible to detect the flow of water (liquid) in a fine part of a plant with high accuracy. By setting the inter-axial distance W within the aforementioned range, water dynamics can be measured with high accuracy while the probes 10, 20A, and 20B are installed on a fine point of a plant such as a new branch distal end.

All the probes 10, 20A, 20B, 30A, and 30B may be separated by the same inter-axial distance W or may be separated by the different inter-axial distances W.

By measuring water dynamics in a plant using the plant water dynamics sensor 1, a plant can be supplied with water or replenished with nutrients at appropriate times that depend on the growing status of the plant. This can contribute to increase in harvest of crops or fruit, and the like. Further, water quantity in a new branch distal end or a pedicel of a plant can be measured, so that water supply can be controlled properly (water resource can be used effectively). This achieves high-value added cultivation of fruit in terms of a high quality (high sugar content in a fruit) or stable production (equal quality), for example.

<Second Embodiment>

A plant water dynamics sensor 2 according to a second embodiment of this invention is described next.

The plant water dynamics sensor 2 of this embodiment is suitably used particularly for measuring the direction and the flow rate (flow speed) of a xylem flow.

Figure 8:
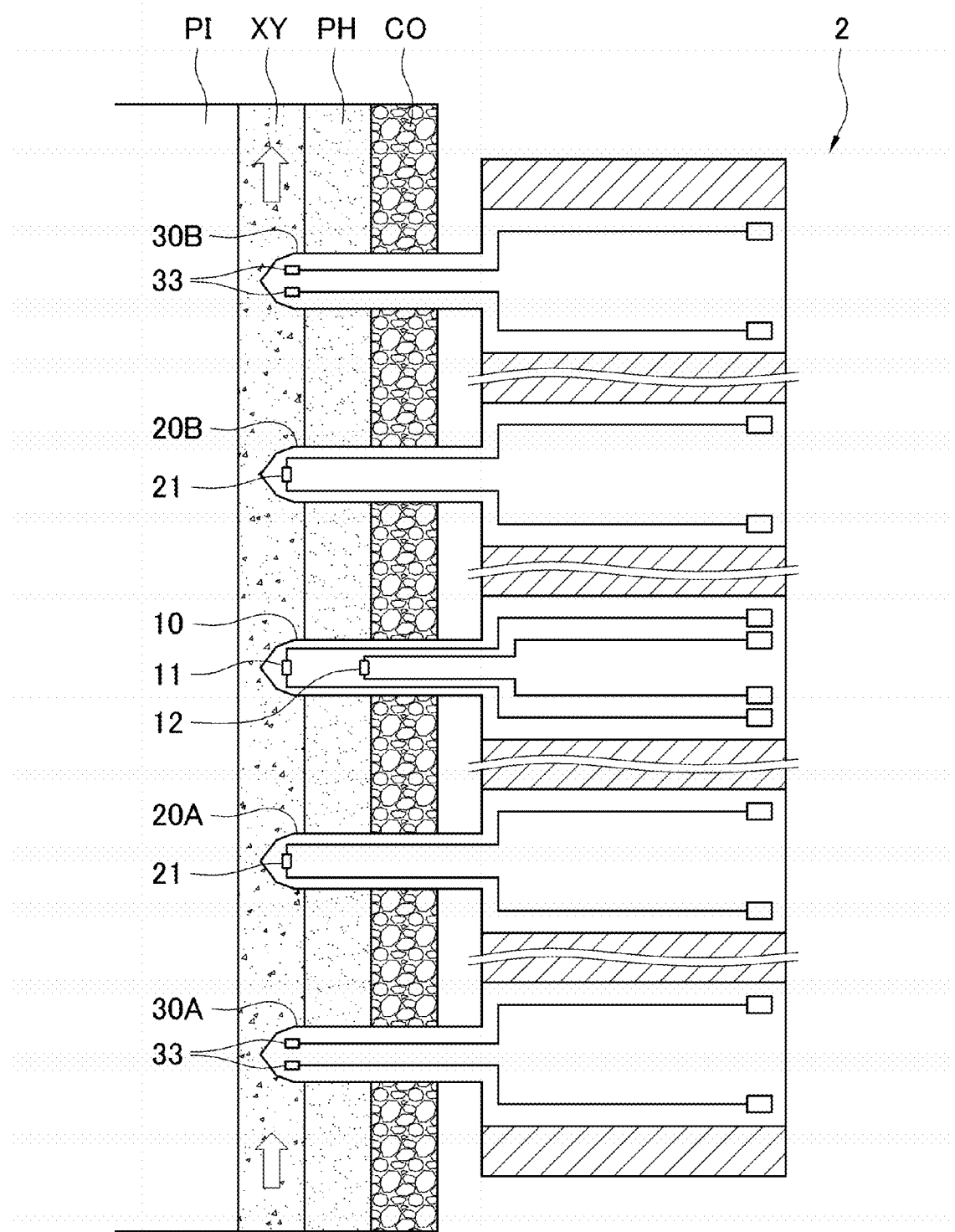
FIG. 8 is an explanatory view schematically showing usage of a plant water dynamics sensor in an enlarged manner according to a second embodiment.

As shown in FIG. 8, in the plant water dynamics sensor 2, all the probes 10, 20A, 20B, 30A, and 30B of the plant water dynamics sensor 1 according to the first embodiment are formed into the same length. Regarding the dimension of each of the probes 10, 20A, 20B, 30A, and 30B, a length is 400 µm and a width is 200 µm, for example.

All the probes 10, 20A, 20B, 30A, and 30B have the same length. The temperature sensor 11 is provided at the tip portion of the heater-equipped temperature probe 10. The temperature sensor 21 is provided at the tip portion of each of the temperature probes 20A and 20B. The electrical resistance measurement electrode 33 is provided at the tip portion of each of the electrical resistance probes 30A and 30B. Thus, the temperature sensors 11 and 21 and the electrical resistance measurement electrode 33 are arranged at the same level in a direction of sticking into a plant as a measurement target.

By arranging the temperature sensors 11 and 21 and the electrical resistance measurement electrode 33 at the same level in this way, while the probes 10, 20A, 20B, 30A, and 30B are stuck into a plant and the electrical resistance measurement electrode 33 is arranged in a position at the xylem XY in the plant, each of the temperature sensors 11 and 21 is arranged in a position at the xylem XY in the plant.

The structure of the plant water dynamics sensor 2 is the same in the other respects as that of the plant water dynamics sensor 1 according to the first embodiment. Thus, common members are identified by the same signs and description of these members will be omitted.

The plant water dynamics sensor 2 can be attached to a new branch distal end of a plant as a measurement target by sticking all the probes 10, 20A, 20B, 30A, and 30B into a fine point of the plant. At this time, each of the temperature sensors 11 and 21 can be arranged correctly in a position at the xylem XY by sticking each of the probes 10, 20A, 20B, 30A, and 30B to a depth at which the xylem XY is detected by the electrical resistance probes 30A and 30B. In this way, attachment of the plant water dynamics sensor 2 is facilitated and a xylem flow can be measured with high accuracy in terms of its flow rate, and the like.

Further, by sticking each of the probes 10, 20A, 20B, 30A, and 30B to a depth in a plant at which the two electrical resistance probes 30A and 30B detect the xylem XY, the temperature sensors 11 and 21 can be aligned along the xylem XY.

By actuating the heater 12 of the heater-equipped temperature probe 10 and comparing temperatures measured at the two temperature probes 20A and 20B, the direction of a xylem flow can be specified. Further, the flow rate (flow speed) of the xylem flow can be measured based on a temperature difference between the temperature probe 20A (20B) at a lower temperature out of the two temperature probes 20A and 20B and the heater-equipped temperature probe 10.

<Third Embodiment>

A plant water dynamics sensor 3 according to a third embodiment of this invention is described next.

The plant water dynamics sensor 3 of this embodiment is suitably used particularly for measuring the flow rate (flow speed) of a xylem flow.

Figure 9:
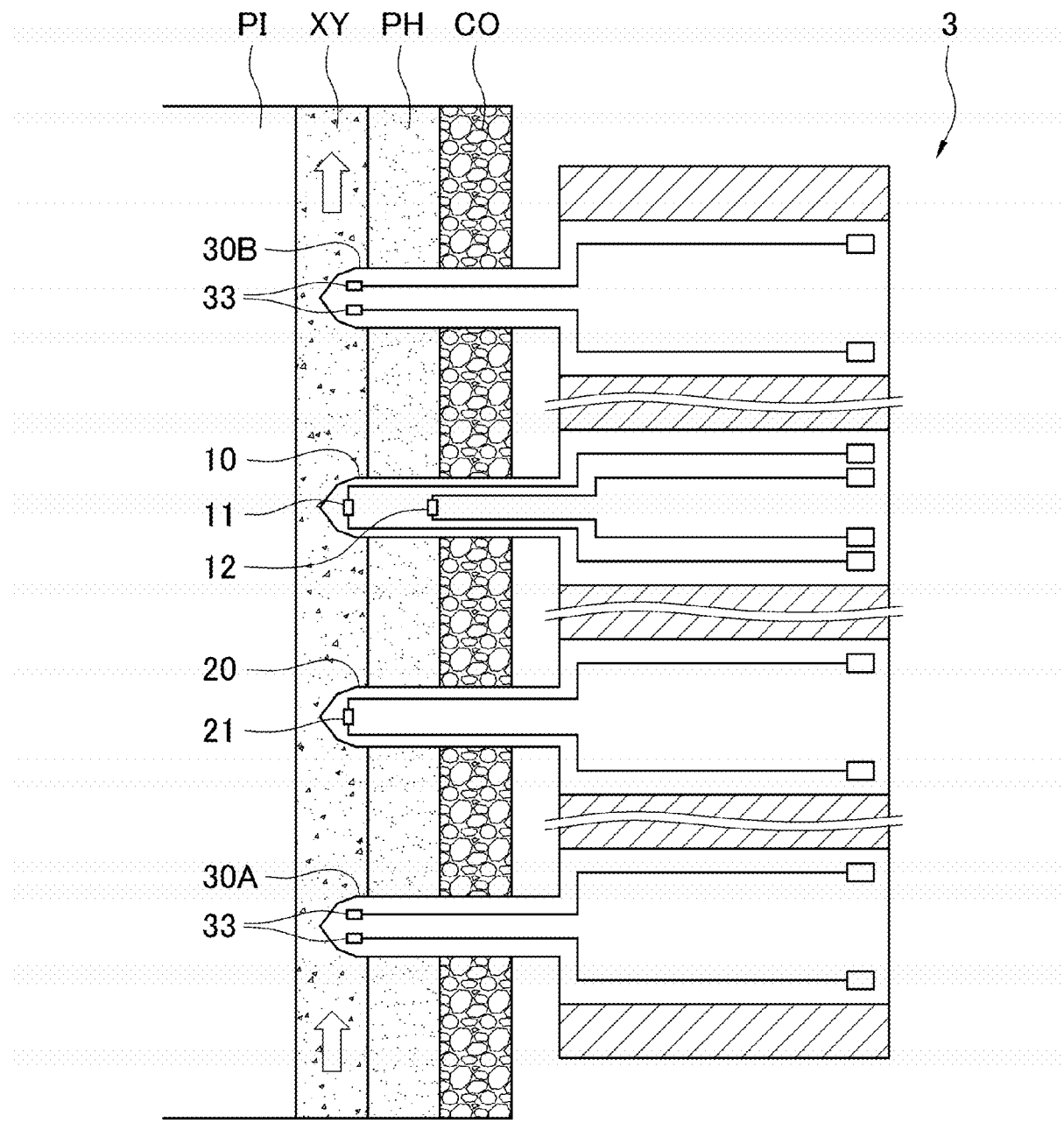
FIG. 9 is an explanatory view schematically showing usage of a plant water dynamics sensor in an enlarged manner according to a third embodiment.

As shown in FIG. 9, one temperature probe 20 of the plant water dynamics sensor 2 according to the second embodiment is provided in the plant water dynamics sensor 3. Specifically, the plant water dynamics sensor 3 includes one heater-equipped temperature probe 10, one temperature probe 20, and the electrical resistance probes 30A and 30B in a pair.

All the probes 10, 20, 30A, and 30B have the same length. The temperature sensors 11 and 21 are provided at the respective tip portions of the heater-equipped temperature probe 10 and the temperature probe 20. The electrical resistance measurement electrode 33 is provided at the tip portion of each of the electrical resistance probes 30A and 30B. Thus, the temperature sensors 11 and 21 and the electrical resistance measurement electrode 33 are arranged at the same level in a direction of sticking into a plant as a measurement target.

The structure of the plant water dynamics sensor 3 is the same in the other respects as that of the plant water dynamics sensor 1 according to the first embodiment. Thus, common members are identified by the same signs and description of these members will be omitted.

The plant water dynamics sensor 3 can be attached to a new branch distal end of a plant as a measurement target by sticking all the probes 10, 20, 30A, and 30B into a fine point of the plant. At this time, the temperature probe 20 is arranged on an upstream side and the heater-equipped temperature probe 10 is arranged on a downstream side of a xylem flow. The xylem flow is generally known to be from a root toward a distal end of the plant. This explains why it is reasonable to arrange the temperature probe 20 to be closer to the root and the heater-equipped temperature probe 10 to be closer to the distal end of the plant.

By sticking each of the probes 10, 20, 30A, and 30B to a depth in a plant at which the electrical resistance probes 30A and 30B detect the xylem XY, each of the temperature sensors 11 and 21 can be arranged correctly in a position at the xylem XY. In this way, attachment of the plant water dynamics sensor 3 is facilitated and a xylem flow can be measured with high accuracy in terms of its flow rate, and the like.

Further, by sticking each of the probes 10, 20, 30A, and 30B to a depth in a plant at which the two electrical resistance probes 30A and 30B detect the xylem XY, the temperature sensors 11 and 21 can be aligned along the xylem XY.

By actuating the heater 12 of the heater-equipped temperature probe 10, the flow rate (flow speed) of a xylem flow can be measured based on a temperature difference between the heater-equipped temperature probe 10 and the temperature probe 20.

<Fourth Embodiment>

A plant water dynamics sensor 4 according to a fourth embodiment of this invention is described next.

The plant water dynamics sensor 4 of this embodiment is suitably used particularly for measuring the direction and the flow rate (flow speed) of a phloem flow.

Figure 10:
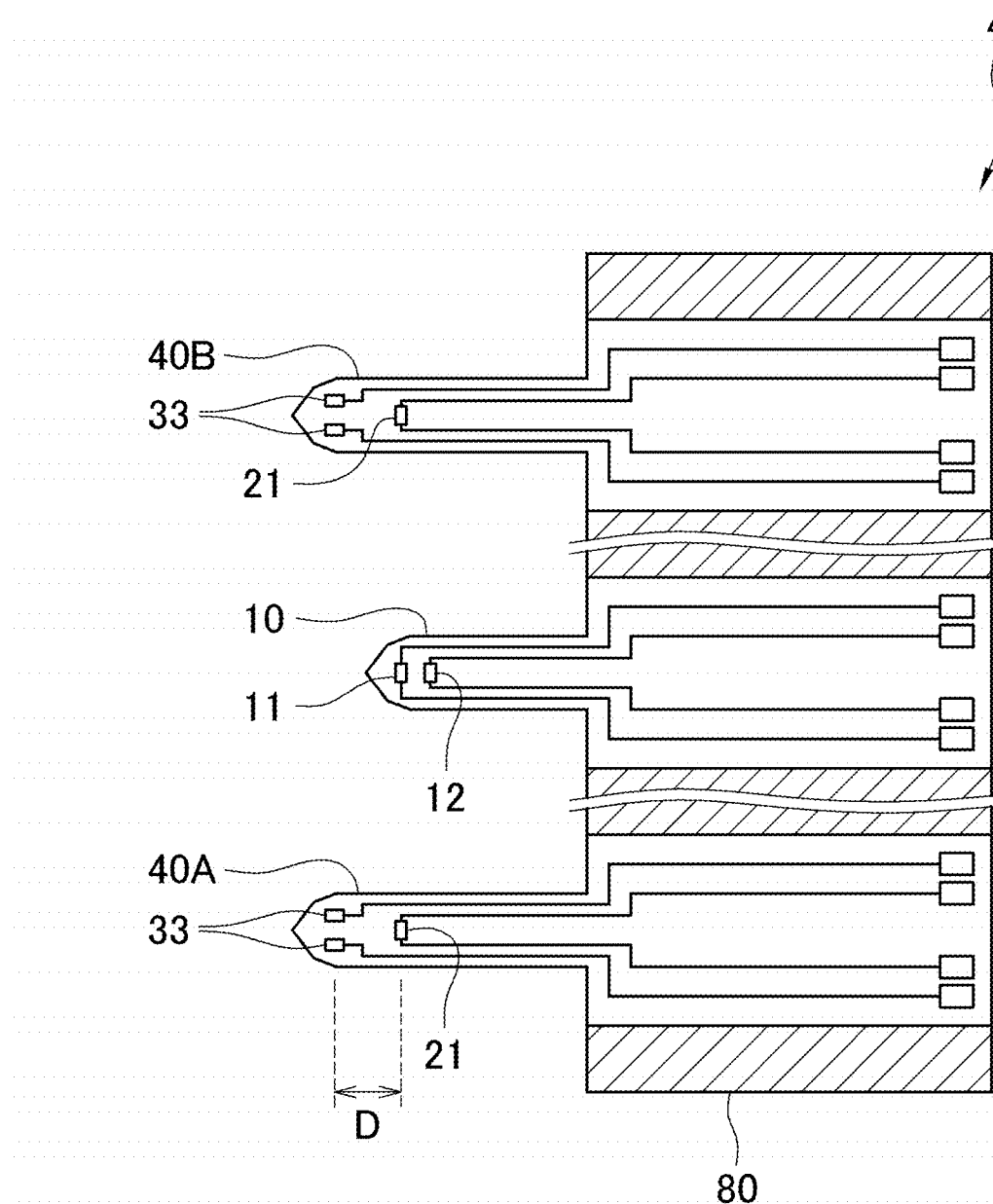
FIG. 10 is a plan view of a plant water dynamics sensor according to a fourth embodiment.

As shown in FIG. 10, the plant water dynamics sensor 4 includes an electrical resistance and temperature probe 40A and an electrical resistance and temperature probe 40B formed by integrating the electrical resistance probe 30A and the temperature probe 20A and integrating the electrical resistance probe 30B and the temperature probe 20B respectively of the plant water dynamics sensor 1 according to the first embodiment. Specifically, the plant water dynamics sensor 4 includes one heater-equipped temperature probe 10, and the electrical resistance and temperature probes 40A and 40B in a pair.

Regarding the dimension of the heater-equipped temperature probe 10, a length is 300 µm and a width is 200 µm, for example. Regarding the dimension of each of the electrical resistance and temperature probes 40A and 40B, each of these probes is formed into a length larger than that of the heater-equipped temperature probe 10 and has a length of 400 µm and a width of 200 µm, for example.

The temperature sensor 11 is provided at the tip portion of the heater-equipped temperature probe 10. Further, the electrical resistance measurement electrodes 33 and 33 in a pair are provided at the tip portion of each of the electrical resistance and temperature probes 40A and 40B. The temperature sensor 21 is provided at each of the electrical resistance and temperature probes 40A and 40B at the same level as the temperature sensor 11 of the heater-equipped temperature probe 10 in a direction of sticking into a plant. Specifically, a level in the direction of sticking into a plant as a measurement target differs by the distance D between the electrical resistance measurement electrode 33 and each of the temperature sensors 11 and 21.

The structure of the plant water dynamics sensor 4 is the same in the other respects as that of the plant water dynamics sensor 1 according to the first embodiment. Thus, common members are identified by the same signs and description of these members will be omitted.

The plant water dynamics sensor 4 can be attached to a new branch distal end of a plant as a measurement target by sticking all the probes 10, 40A, and 40B into a fine point of the plant. At this time, each of the temperature sensors 11 and 21 can be arranged correctly in a position at the phloem PH by sticking each of the probes 10, 40A, and 40B to a depth at which the xylem XY is detected by the electrical resistance and temperature probes 40A and 40B. In this way, attachment of the plant water dynamics sensor 4 is facilitated and a phloem flow can be measured with high accuracy in terms of its flow rate, and the like.

By actuating the heater 12 of the heater-equipped temperature probe 10 and comparing temperatures measured at the two electrical resistance and temperature probes 40A and 40B, the direction of a phloem flow can be specified. Further, the flow rate (flow speed) of the phloem flow can be measured based on a temperature difference between the electrical resistance and temperature probe 40A (40B) at a lower temperature out of the two electrical resistance and temperature probes 40A and 40B and the heater-equipped temperature probe 10.

This embodiment includes the probes 10, 40A, and 40B of a reduced number. This can reduce the size of the plant water dynamics sensor 4. The small number of the probes 10, 40A, and 40B can alleviate damage (failure) of a plant further.

<Fifth Embodiment>

A plant water dynamics sensor 5 according to a fifth embodiment of this invention is described next.

The plant water dynamics sensor 5 of this embodiment is suitably used particularly for measuring the direction and the flow rate (flow speed) of a xylem flow.

Figure 11:
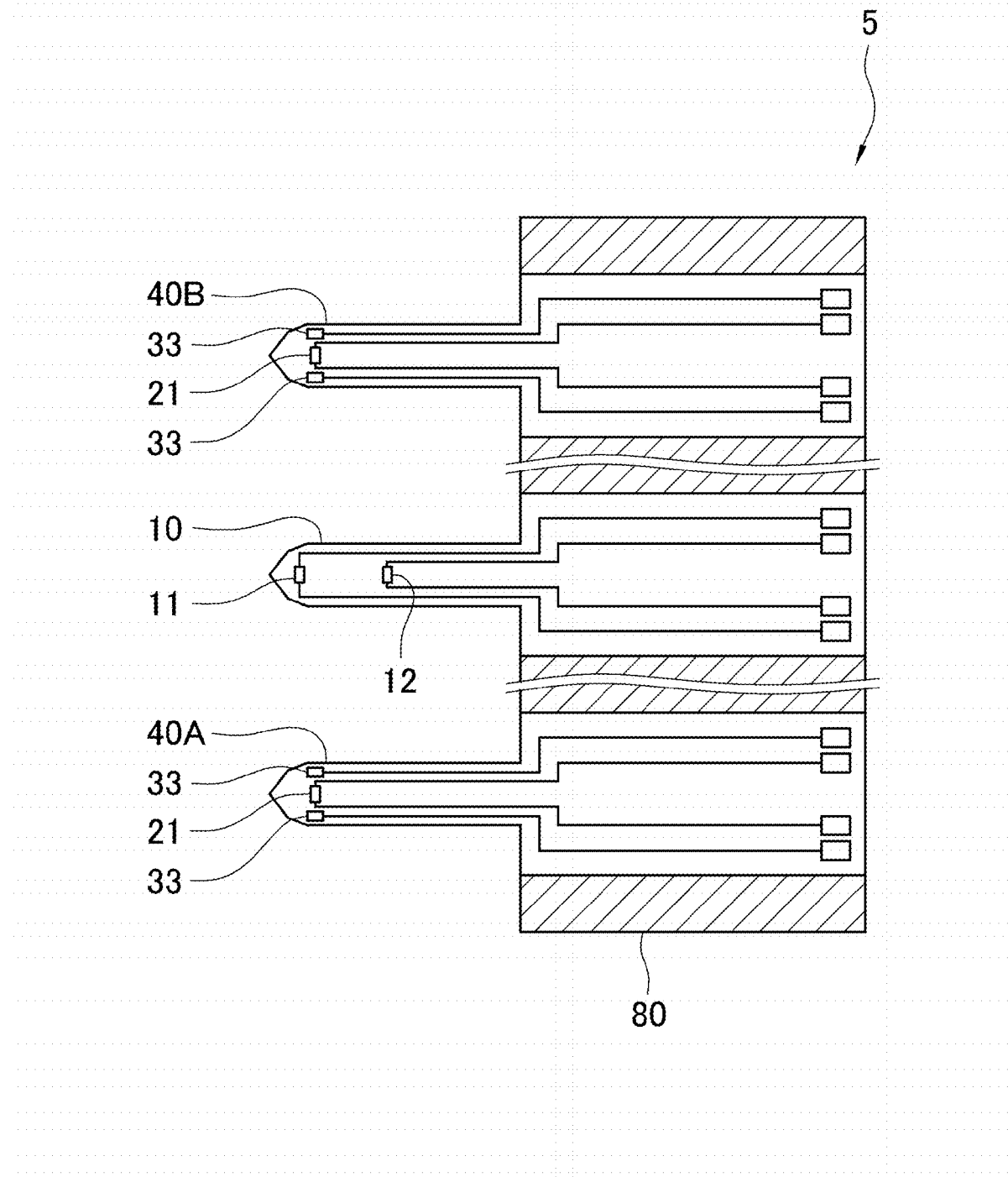
FIG. 11 is a plan view of a plant water dynamics sensor according to a fifth embodiment.

As shown in FIG. 11, the plant water dynamics sensor 5 includes the electrical resistance and temperature probes 40A and 40B formed by integrating the electrical resistance probe 30A and the temperature probe 20A and integrating the electrical resistance probe 30B and the temperature probe 20B respectively of the plant water dynamics sensor 2 according to the second embodiment. Specifically, the plant water dynamics sensor 5 includes one heater-equipped temperature probe 10, and the electrical resistance and temperature probes 40A and 40B in a pair.

The heater-equipped temperature probe 10 and the electrical resistance and temperature probes 40A and 40B have the same dimension. For example, the length and the width of each of these probes are 400 µm and 200 µm respectively. The temperature sensor 11 is provided at the tip portion of the heater-equipped temperature probe 10. The electrical resistance measurement electrodes 33 and 33 in a pair and the temperature sensor 21 are provided at the tip portion of each of the electrical resistance and temperature probes 40A and 40B. Specifically, the electrical resistance measurement electrode 33 and the temperature sensors 11 and 21 are arranged at the same level in a direction of sticking into a plant as a measurement target.

The structure of the plant water dynamics sensor 5 is the same in the other respects as that of the plant water dynamics sensor 2 according to the second embodiment. Thus, common members are identified by the same signs and description of these members will be omitted.

The plant water dynamics sensor 5 can be attached to a new branch distal end of a plant as a measurement target by sticking all the probes 10, 40A, and 40B into a fine point of the plant. At this time, each of the temperature sensors 11 and 21 can be arranged correctly in a position at the xylem XY by sticking each of the probes 10, 40A, and 40B to a depth at which the xylem XY is detected by the electrical resistance and temperature probes 40A and 40B. In this way, attachment of the plant water dynamics sensor 5 is facilitated and a xylem flow can be measured with high accuracy in terms of its flow rate, etc.

By actuating the heater 12 of the heater-equipped temperature probe 10 and comparing temperatures measured at the two electrical resistance and temperature probes 40A and 40B, the direction of a xylem flow can be specified. Further, the flow rate (flow speed) of the xylem flow can be measured based on a temperature difference between the electrical resistance and temperature probe 40A (40B) at a lower temperature out of the two electrical resistance and temperature probes 40A and 40B and the heater-equipped temperature probe 10.

This embodiment includes the probes 10, 40A, and 40B of a reduced number. This can reduce the size of the plant water dynamics sensor 5. The small number of the probes 10, 40A, and 40B can alleviate damage (failure) of a plant further.

<Sixth Embodiment>

In the aforementioned fourth and fifth embodiments, the electrical resistance probe 30 and the temperature probe 20 are formed as an integrated probe. Alternatively, the electrical resistance probe 30 and the heater-equipped temperature probe 10 may be formed as an integrated probe.

This embodiment can also reduce the number of probes, so that the size of a plant water dynamics sensor can be reduced. The small number of probes can alleviate damage (failure) of a plant further.

<Seventh Embodiment>

A plant water dynamics sensor 7 according to a seventh embodiment of this invention is described next.

The plant water dynamics sensor 7 of this embodiment is used suitably for analyzing a nutritive substance in sap.

Figure 12:
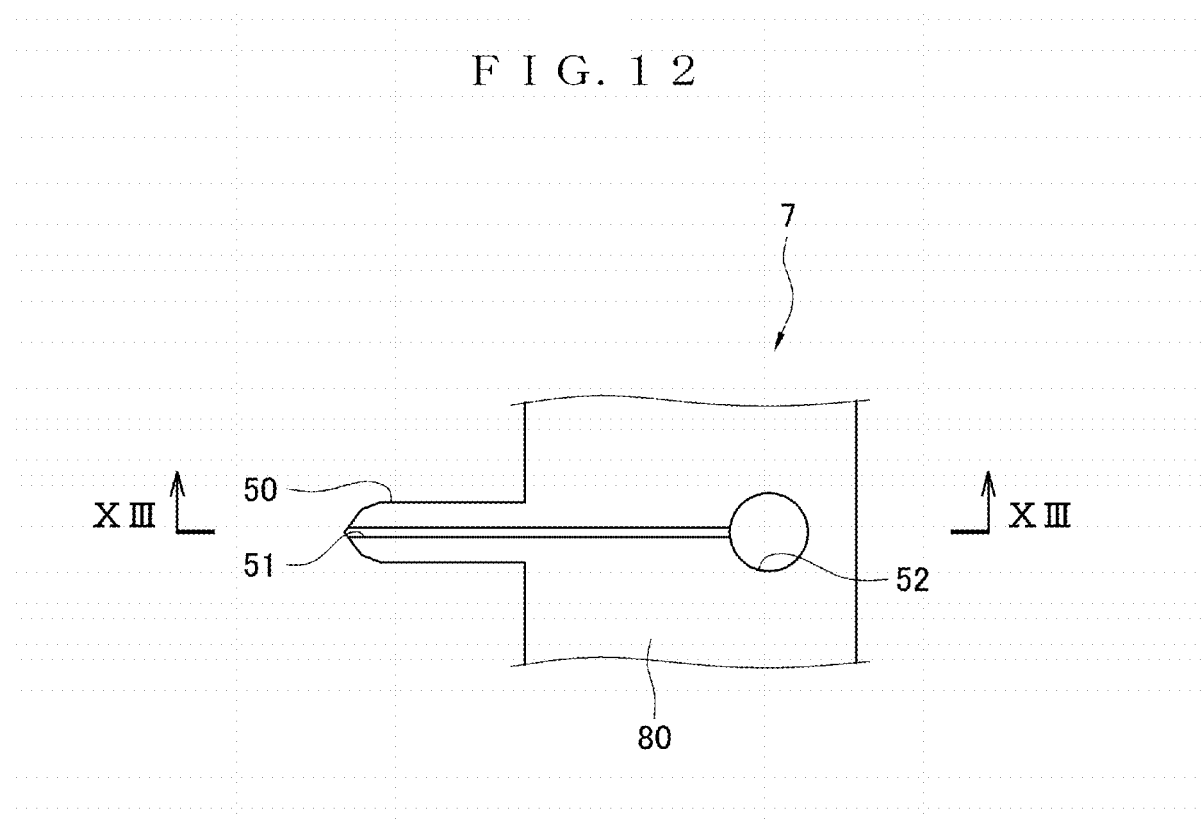
FIG. 12 is a plan view of a plant water dynamics sensor according to a seventh embodiment.
Figure 13:
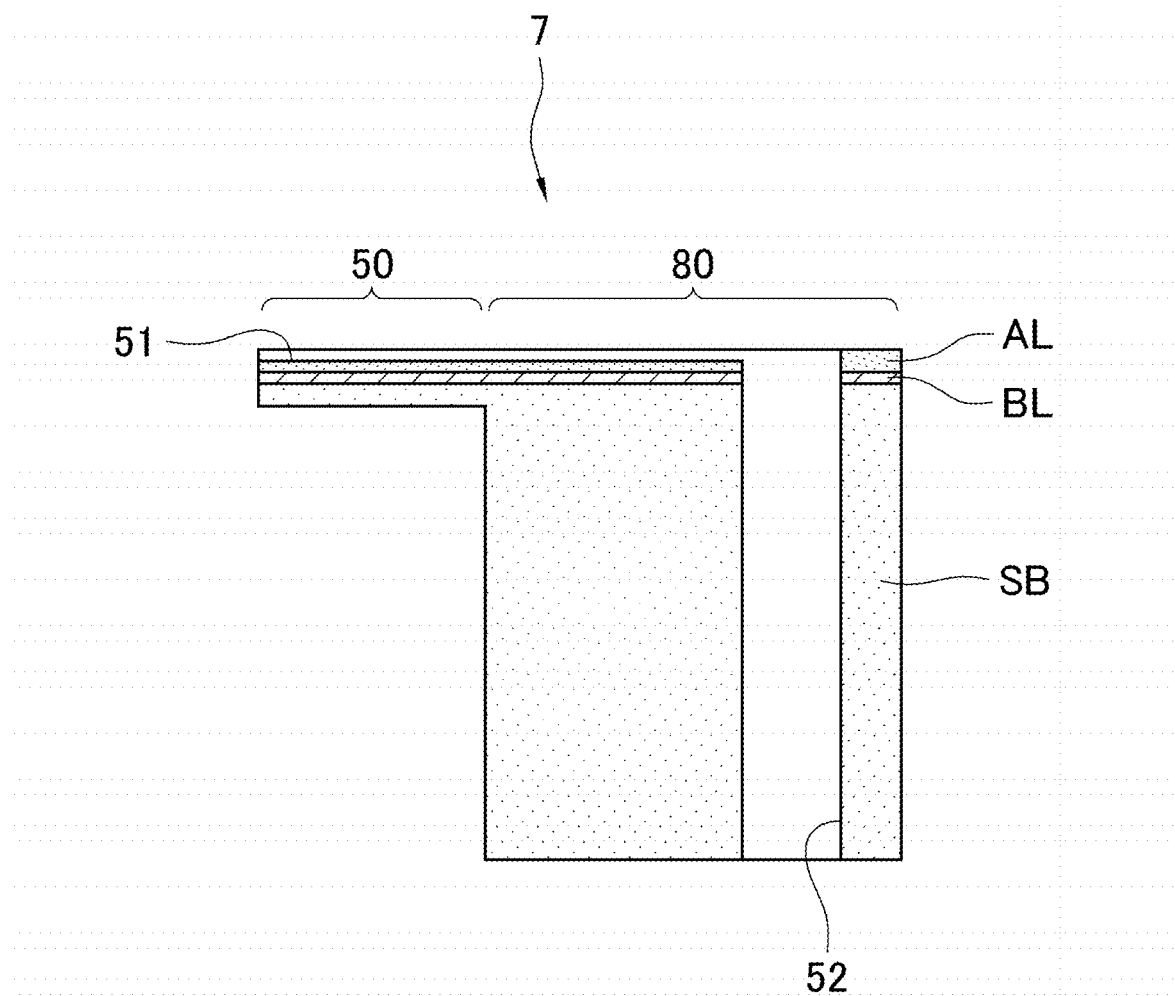
FIG. 13 is a sectional view taken along arrow line XIII-XIII of FIG. 12.

As shown in FIGS. 12 and 13, the plant water dynamics sensor 7 includes a trapping probe 50. Although not shown in the drawings, like those of the aforementioned first to sixth embodiments, the plant water dynamics sensor 7 includes the heater-equipped temperature probe 10, the temperature probe 20, and the electrical resistance probe 30. While the trapping probe 50 and the other probes 10, 20, and 30 are aligned together parallel to each other in the same horizontal plane, the trapping probe 50 is supported on the support 80 at its base end. By sticking these probes 10, 20, 30, and 50 into a plant, the plant water dynamics sensor 7 is installed on the plant.

The trapping probe 50 has the substantially same dimension as the other probes 10, 20, and 30. A groove-like flow channel 51 is formed in a surface of the trapping probe 50, specifically, in a surface of the active layer AL to extend along the center of the axis of the trapping probe 50. A through hole 52 is formed in the support 80 to penetrate the support 80 from front to back. The flow channel 51 is formed to extend from the tip toward the base end of the trapping probe 50 and reaches the through hole 52 in the support 80.

The flow channel 51 and the through hole 52 are formed for example by the following method. First, a resist pattern for the flow channel 51 and the through hole 52 are formed on the surface of the trapping probe 50 and that of the support 80. Next, the flow channel 51 and the through hole 52 are formed by wet etching or dry etching. Then, the resist pattern, which is no longer necessary, is removed.

By sticking the trapping probe 50 into a plant as a measurement target and arranging the tip of the trapping probe 50 in the xylem XY in the plant, xylem sap flows into the flow channel 51 and is guided into the through hole 52. By arranging the tip of the trapping probe 50 in the phloem PH in the plant, phloem sap flows into the flow channel 51 and is guided into the through hole 52. The sap (xylem sap or phloem sap) guided into the through hole 52 can be collected for example by a pump connected to the back surface of the support 80. In this way, the sap in the plant can be trapped through the flow channel 51.

The trapped sap can be analyzed in terms of a nutritive substance therein and the like, by being carried for example to a laboratory and analyzed by a device such as a liquid chromatography. As described above, sap can be trapped using the trapping probe 50, so that the plant water dynamics sensor 7 is usable for analyzing the nutritive substance in the sap.

<Eighth Embodiment>

In the seventh embodiment, the trapping probe 50 is formed as a probe independent of the other probes 10, 20, and 30. Alternatively, the trapping probe 50 may be formed as a probe integrated with the heater-equipped temperature probe 10, the temperature probe 20, or the electrical resistance probe 30.

Figure 14:
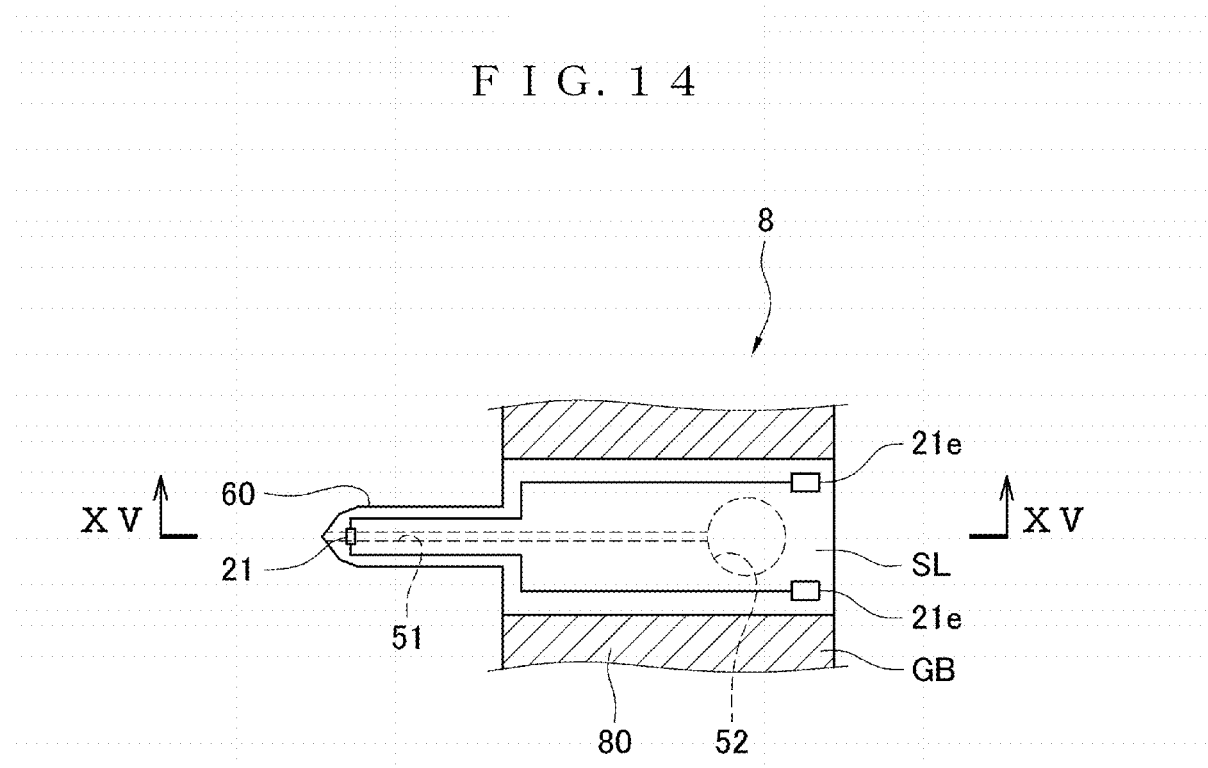
FIG. 14 is a plan view of a plant water dynamics sensor according to an eighth embodiment.
Figure 15:
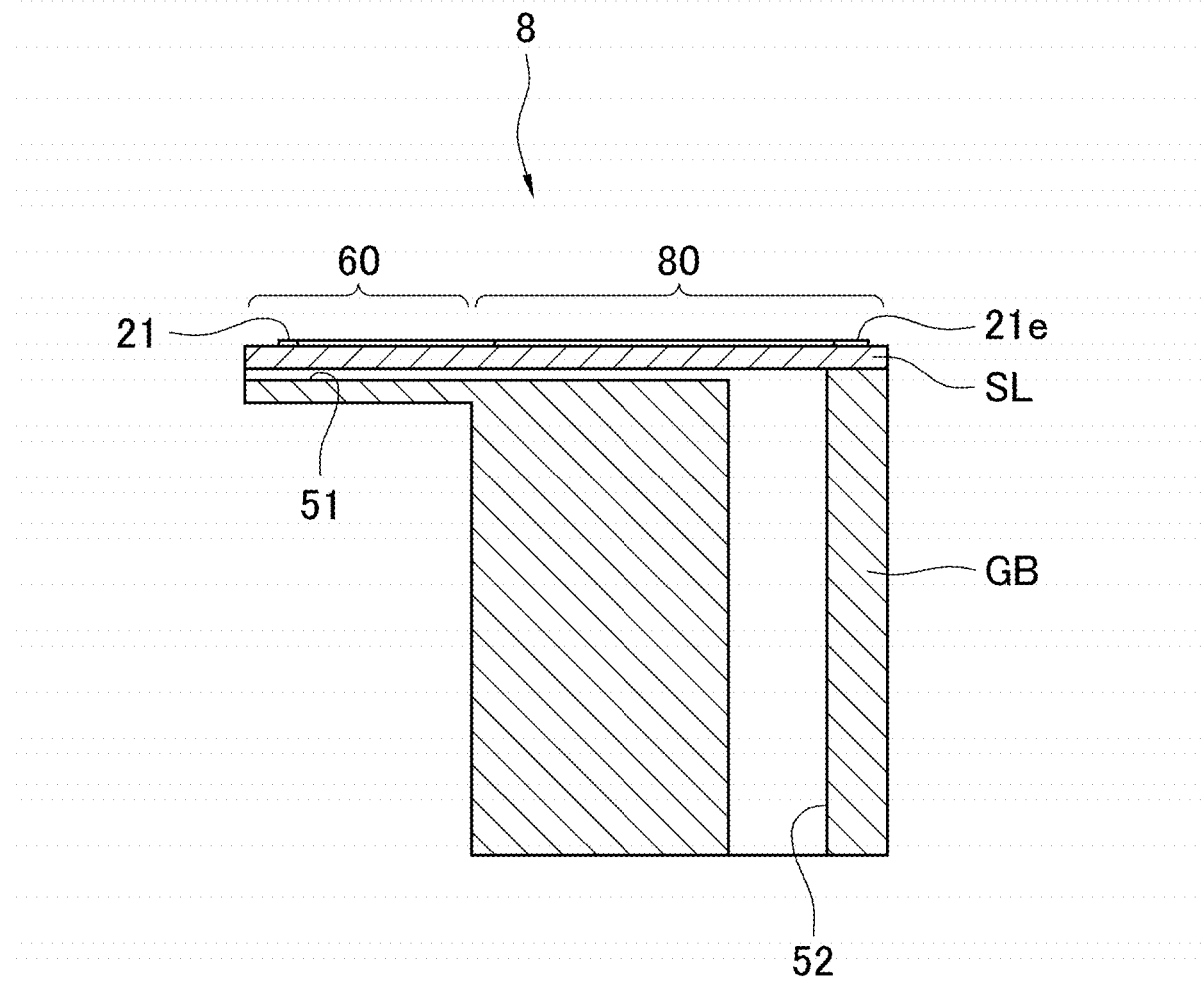
FIG. 15 is a sectional view taken along arrow line XV-XV of FIG. 14.

An example shown in FIGS. 14 and 15 includes a trapping and temperature probe 60 formed by integrating the trapping probe 50 and the temperature probe 20. The flow channel 51 is formed inside the trapping and temperature probe 60 to extend along the center of the axis of the trapping and temperature probe 60. Specifically, the trapping and temperature probe 60 is formed into a hollow needle shape. The temperature sensor 21 and the interconnect lines for connection to the electrode pads 21e are placed along a surface of the trapping and temperature probe 60.

The structure of a plant water dynamics sensor 8 of this embodiment includes a borosilicate glass substrate GB and a silicon substrate SL bonded together. A groove for the flow channel 51 is formed in a surface of the borosilicate glass substrate GB and then the silicon substrate SL is bonded on the borosilicate glass substrate GB, thereby forming the flow channel 51 encompassed by the trapping and temperature probe 60. The through hole 52 continuous with the flow channel 51 is also formed in the borosilicate glass substrate GB.

The trapping and temperature probe 60 is formed by providing the temperature sensor 21 and the interconnect lines on a surface of the silicon substrate SL. An integrated probe of the trapping probe 50 and the heater-equipped temperature probe 10 or an integrated probe of the trapping probe 50 and the electrical resistance probe 30 can be formed by changing a member to be provided on the surface of the silicon substrate SL.

This embodiment can also reduce the number of probes, so that the size of the plant water dynamics sensor 8 can be reduced. The small number of probes can alleviate damage (failure) of a plant further.

<Other Embodiments>

In the aforementioned embodiments, a probe is formed into a cantilever shape parallel to a surface of the support 80 like a flat plate. Alternatively, a probe may be formed to stand upright on the surface of the support 80. This probe can be formed for example by the following method. First, a resist mask to become a prototype of the shape of the probe is formed on a Si substrate. Then, crystalline anisotropic etching is performed for processing into a conical shape. Next, vertical etching is performed to form a cylindrical shape. Finally, a mask material, which is no longer necessary, is removed to form the probe.

In the aforementioned embodiments, a compact sensor is formed using MEMS technology for measurement of water dynamics in a fine point of a plant such as a new branch distal end. If a sensor is intended to be used for measuring water dynamics in a trunk of a tree, for example, the sensor can be formed into a dimension comparable to that of a conventional sensor without using MEMS technology.

<Plant Water Dynamics Information Retrieving System>

The aforementioned plant water dynamics sensors 1 to 8 (hereinafter collectively called plant water dynamics sensors 1) become applicable for water supply, replenishment with nutrients (fertilization), etc. of a plant by transmitting measurement data such as data about the flow rate (flow speed) of water (liquid) flowing in a fine point of a plant such as a new branch distal end from the plant water dynamics sensors 1 for example to a server via a line or using a wireless communication unit, etc., and managing the transmitted data in a centralized manner.

The following describes a plant water dynamics information retrieving system used for managing plant water dynamics information measured by a plurality of plant water dynamics sensors 1 in a centralized manner at a server.

Figure 16:
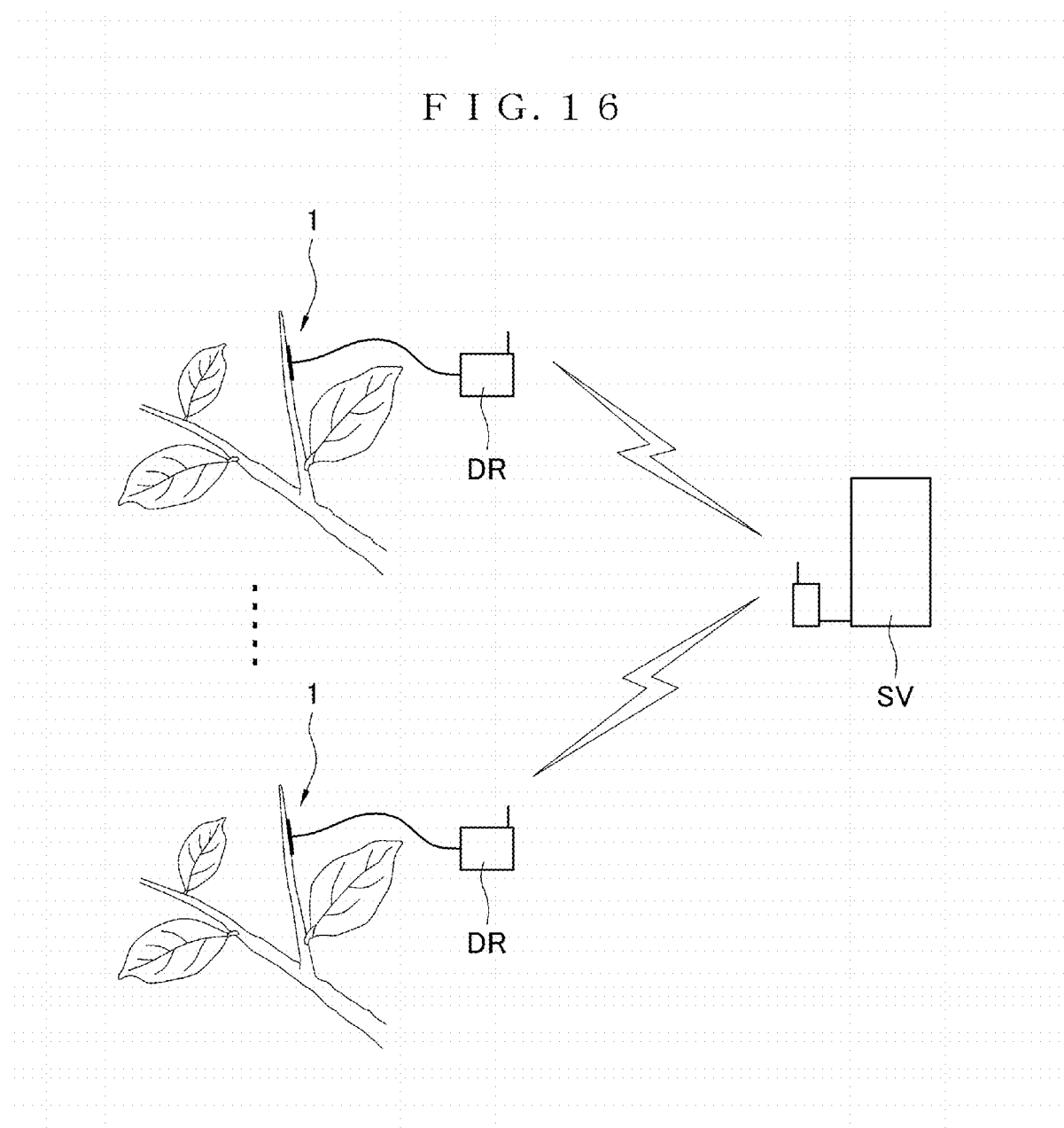
FIG. 16 is an explanatory view schematically showing a plant water dynamics information retrieving system.

As shown in FIG. 16, the plurality of plant water dynamics sensors 1 is attached to a plurality of plants in an agricultural site. The plant water dynamics sensors 1 can be attached to a plurality of points of one plant, to all of these plants, or to some of these plants as a sample.

Each of the plant water dynamics sensors 1 is connected to a data logger DR for power supply and collection of data of various types. The data logger DR includes a built-in wireless communication unit in addition to the aforementioned constant current source 91, voltmeter 92, DC constant voltage source 93, AC source 94, and ammeter 95.

A server SV for centralized management of plant water dynamics information is installed on a building adjacent to the agricultural site. The server SV is also connected to the wireless communication unit, so that the server SV can make wireless communication with the data logger DR.

Each data logger DR transmits measurement data obtained by the corresponding plant water dynamics sensor 1 to the server SV via the wireless communication unit. The server SV manages the received measurement data in a centralized manner. The measurement data is applicable for water supply, replenishment with nutrients (fertilization), etc. of a plant by being analyzed by the server SV.

EXAMPLE

The following tests were conducted to verify the effectiveness of the plant water dynamics sensor according to this invention.

(Experiment on Temperature Characteristic of Temperature Sensor)

First, experiment on the temperature characteristics of a temperature sensor was conducted.

A result thereof confirms that the temperature sensor can make measurement at a sensitivity of −5.6 mv/° C. in a range from 16.6 to 75.7° C.

(Temperature Rise Experiment Using Heater)

Next, temperature rise experiment was conducted using a heater.

A result thereof confirms that the heater can raise a temperature from normal temperature to 67° C. in response to application of a DC voltage of 310 mW.

(Experiment on Position Detection)

Next, experiment on position detection using an electrical resistance was conducted.

An experimental device shown in FIG. 17 was prepared. The experimental device includes needle-like electrodes in a pair, a micrometer, and a multimeter. The needle-like electrodes have a diameter of 0.55 mm. The needle-like electrodes in a pair were stuck into a plant using the micrometer and an electrical resistance between the needle-like electrodes was measured using the multimeter.

FIG. 18 is a graph showing a relationship between a sticking depth of the needle-like electrodes and an electrical resistance. As understood from FIG. 18, an electrical resistance measured at a depth in a range from about 150 to about 300 μm is lower than that measured at a depth in a different range. Xylem sap flowing in a xylem contains minerals, so that it has the property of being lower in electrical resistance than water in the other parts. Thus, this range where an electrical resistance is low is considered to correspond to the range of a xylem. This result confirms that an electrical resistance measured using an electrical resistance probe is usable for detecting the position of a xylem.

(Experiment of Measuring Direction and Flow Rate of Sap Flow)

Next, experiment of measuring the detection and the flow rate of a sap flow was conducted.

The experiment was conducted using an artificial plant experimental system shown in FIG. 19. In this artificial plant experimental system, an artificial vascular bundle was formed by flowing water into a silicone tube (of a diameter of 1 mm and a thickness of 0.2 mm) using a micro syringe pump. The probes of the plant water dynamics sensor 1 according to the aforementioned first embodiment were stuck into the artificial vascular bundle. A flow rate in the silicone tube can be controlled precisely using the micro syringe pump. The plant water dynamics sensor was connected to a constant current source for a temperature sensor, a DC source for a heater, and a data logger for retrieval of data.

Figure 20:
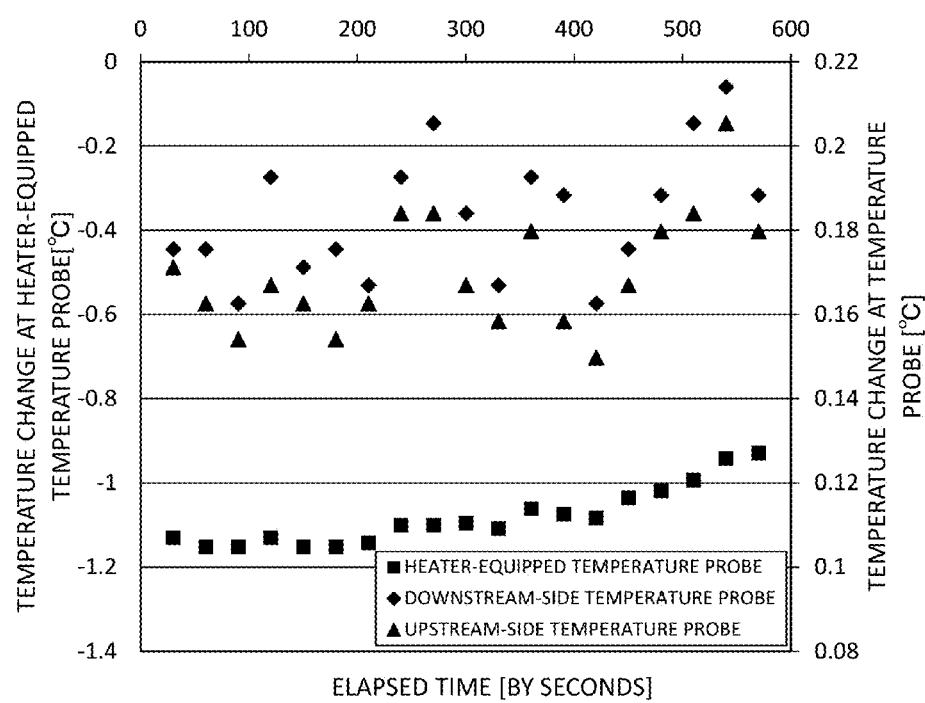
FIG. 20 is a graph showing temporal temperature change at a heater-equipped temperature probe and that at a temperature probe.

FIG. 20 is a graph showing temporal temperature change at the heater-equipped temperature probe 10 and those at the temperature probes 20A and 20B from start of temperature measurement while a flow rate (average speed of sap flow) in the syringe pump was set at 100 μm/s. As understood from FIG. 20, a temperature at the temperature probe 20A on an upstream side is lower than a temperature at the temperature probe 20B on a downstream side. This result confirms that the direction of a sap flow can be specified by comparing temperatures measured at the two temperature probes 20A and 20B.

FIG. 21 is a graph showing a relationship between a flow rate (average speed u of sap flow) in the micro syringe pump and a K value. The K value mentioned herein is obtained from a temperature difference between the heater-equipped temperature probe 10 and the temperature probe 20A on an upstream side (see formula 1). By performing curve fitting on measured K values, the factors $1/\alpha$ and $1/\beta$ in formula 1 were determined to be 0.095 and 0.828 respectively. This result confirms that the flow rate of a sap flow can be measured.

Figure 22:
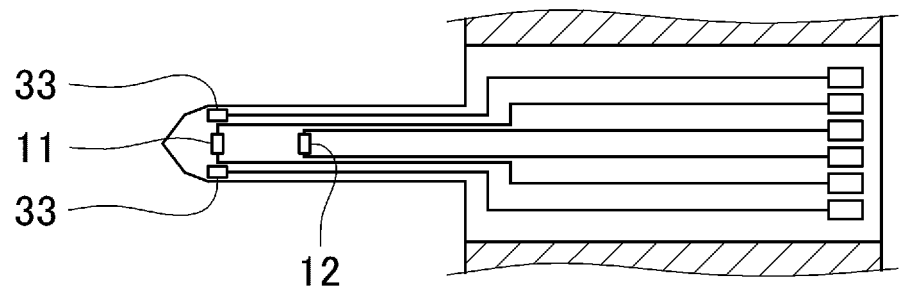
FIG. 22 is a plan view of an electrical resistance probe according to another embodiment, which is formed as a single probe including a temperature sensor and a heater of a heater-equipped temperature probe.

FIG. 22 is a plan view of an electrical resistance probe according to another embodiment, which is formed as a single probe including a temperature sensor and a heater of a heater-equipped temperature probe. FIG. 23 is a plan view of a trapping probe according to still another embodiment, which is formed as a single probe including a temperature sensor and a heater of a heater-equipped temperature probe. FIG. 24 is a plan view of a trapping probe according to still further embodiment, which is formed as a single probe including an electrical resistance measurement electrode of an electrical resistance probe.

INDUSTRIAL APPLICABILITY

The plant water dynamics sensor of this invention is used suitably for measuring water dynamics in a plant.

The invention claimed is:

1. A plant water dynamics sensor used for measuring water dynamics in a plant, comprising:
   at least one heater-equipped temperature probe including a temperature sensor and a heater;
   at least one temperature probe including a temperature sensor;
   at least one electrical resistance probe including an electrical resistance measurement electrode; and
   a support that supports the at least one heater-equipped temperature probe, the at least one temperature probe, and the at least one electrical resistance probe while the at least one heater-equipped temperature probe, the at least one temperature probe, and the at least one electrical resistance probe are aligned parallel to each other.

2. The plant water dynamics sensor according to claim 1, wherein the electrical resistance measurement electrode is arranged at a different aligned position from the temperature sensors of the at least one heater-equipped temperature probe and the at least one temperature probe in a direction of sticking into the plant, and while the electrical resistance measurement electrode is arranged in a position at a xylem in the plant, each of the temperature sensors of the at least one heater-equipped temperature probe and the at least one temperature probe is arranged in a position at a phloem in the plant.

3. The plant water dynamics sensor according to claim 1, wherein the temperature sensors of the at least one heater-equipped temperature probe and the at least one temperature probe and the electrical resistance measurement electrode are arranged at the same aligned position in a direction of sticking into the plant.

4. The plant water dynamics sensor according to claim 1, wherein the at least one electrical resistance probe includes two electrical resistance probes.

5. The plant water dynamics sensor according to claim 1, wherein the at least one temperature probe includes two temperature probes, and the two temperature probes are provided in positions where the two temperature probes hold the at least one heater-equipped temperature probe therebetween.

6. The plant water dynamics sensor according to claim 1, wherein the at least one electrical resistance probe is formed as a single probe including the temperature sensor and the heater of the at least one heater-equipped temperature probe or the temperature sensor of the at least one temperature probe.

7. The plant water dynamics sensor according to claim 1, comprising at least one trapping probe including a flow channel into which sap in the plant is to flow.

8. The plant water dynamics sensor according to claim 7, wherein the trapping probe is formed as a single probe including the temperature sensor and the heater of the at least one heater-equipped temperature probe, the temperature sensor of the at least one temperature probe, or the electrical resistance measurement electrode of the at least one electrical resistance probe.

9. The plant water dynamics sensor according to claim 1, wherein the at least one heater-equipped temperature probe, the at least one temperature probe, the at least one electrical resistance probe, and the support are formed of a silicon on insulator (SOI) substrate, and each of the at least one heater-equipped temperature probe, the at least one temperature probe, and the at least one electrical resistance probe is formed in a cantilever shape at an edge of the support.

\* \* \* \* \*